United States Patent
Tran

(10) Patent No.: US 8,084,762 B2
(45) Date of Patent: Dec. 27, 2011

(54) RESISTIVE MEMORY

(76) Inventor: Bao Tran, Saratoga, CA (US)

( * ) Notice: Subject to any disclaimer, the term of this patent is extended or adjusted under 35 U.S.C. 154(b) by 0 days.

(21) Appl. No.: 12/905,069

(22) Filed: Oct. 14, 2010

(65) Prior Publication Data

US 2011/0110141 A1    May 12, 2011

Related U.S. Application Data

(63) Continuation of application No. 12/617,198, filed on Nov. 12, 2009, now Pat. No. 7,864,560.

(51) Int. Cl.
*H01L 45/00* (2006.01)
(52) U.S. Cl. .......... 257/5; 257/2; 257/E45.001; 365/148
(58) Field of Classification Search .................. 257/2, 5, 257/E45.001; 365/148
See application file for complete search history.

(56) References Cited

U.S. PATENT DOCUMENTS

| | | | | |
|---|---|---|---|---|
| 6,548,382 | B1 * | 4/2003 | Henley et al. | 438/526 |
| 6,657,884 | B2 * | 12/2003 | Bocian et al. | 365/151 |
| 6,664,594 | B2 * | 12/2003 | Klodzinski | 257/341 |
| 6,917,084 | B2 * | 7/2005 | Baum et al. | 257/401 |
| 6,992,390 | B2 * | 1/2006 | Edelstein et al. | 257/752 |
| 7,145,824 | B2 * | 12/2006 | Bill et al. | 365/212 |
| 2009/0201716 | A1 * | 8/2009 | Ufert | 365/148 |

* cited by examiner

*Primary Examiner* — Victor A Mandala
(74) *Attorney, Agent, or Firm* — Tran & Associates

(57) ABSTRACT

A memory device includes an array of memory structures disposed in rows and columns and constructed over a substrate, each memory structure comprising a first signal electrode, a second signal electrode, and a resistive layer coupled to the first signal electrode and the second signal electrode; a plurality of word lines connected to the first signal electrodes of a row of memory cells; and a plurality of bit lines connected to the second signal electrodes of a column of memory cells.

19 Claims, 10 Drawing Sheets

RESISTIVE MEMORY

This application is a continuation application from application Ser. No. 12/617,198 filed Nov. 12, 2009, now U.S. Pat. No. 7,864,560, which claims priority to application Ser. No. 12/348,904, now U.S. Pat. No. 7,630,227, which in turn claims priority to application Ser. No. 11/867,566, now U.S. Pat. No. 7,489,537, which is a divisional of Ser. No. 11/064,364, now U.S. Pat. No. 7,330,369, which claims priority to Provisional Application 60/560,053 filed Apr. 6, 2004, the content of which is incorporated by reference.

BACKGROUND

The present invention relates to memory devices.

The success of the PC, networking, and communications-product markets has been driven largely by Moore's Law, which says that IC density doubles every 18 months. Experts predict that CMOS scaling will continue to follow Moore's Law for at least another decade, but potential bottlenecks could derail market success if not solved by new design or device technology. One of these bottlenecks is integrating precision analog and wideband RF circuitry in standard digital CMOS.

Applying Moore's Law to mixed-signal (analog and digital) chips is a significant challenge. Higher transistor density and lower silicon cost allow more complex digital circuitry, but most wireless or wireline communications products require integrating RF, analog, and memory with the digital logic. Advancements in submicron CMOS processing greatly benefit digital logic and memory, but result in poor analog and RF performance. Transistor matching, noise, resistors, capacitors, and inductors drive the density of analog circuits, and these parameters do not necessarily benefit from transistor scaling.

To compound the problem, digital-circuit design continues to benefit from advances in logic synthesis, accelerating the time-to-market of digital products. Analog circuit design has not historically benefited significantly from CAD-tool advances, and remains a hand-crafted art. Consequently, analog circuits will be a limiting factor for mixed-signal SoC, both in terms of the increasingly larger percentage of the die these circuits occupy, and in terms of their design time.

SUMMARY

Systems and methods are disclosed to form a memory device.

In one aspect, a memory device includes an array of memory structures disposed in rows and columns and constructed over a substrate, each memory structure comprising a first signal electrode, a second signal electrode, and a resistive layer coupled to the first signal electrode and the second signal electrode; a plurality of word lines connected to the first signal electrodes of a row of memory cells; and a plurality of bit lines connected to the second signal electrodes of a column of memory cells.

Advantages may include one or more of the following. The system is compact, power efficient, and dense. The molecular electronics in the above system extend the miniaturization that has driven the density and speed advantages of the integrated circuit in accordance with Moore's Law.

DESCRIPTION

Programmable Analog Nano-Array and Nano-Cells

Figure 1:
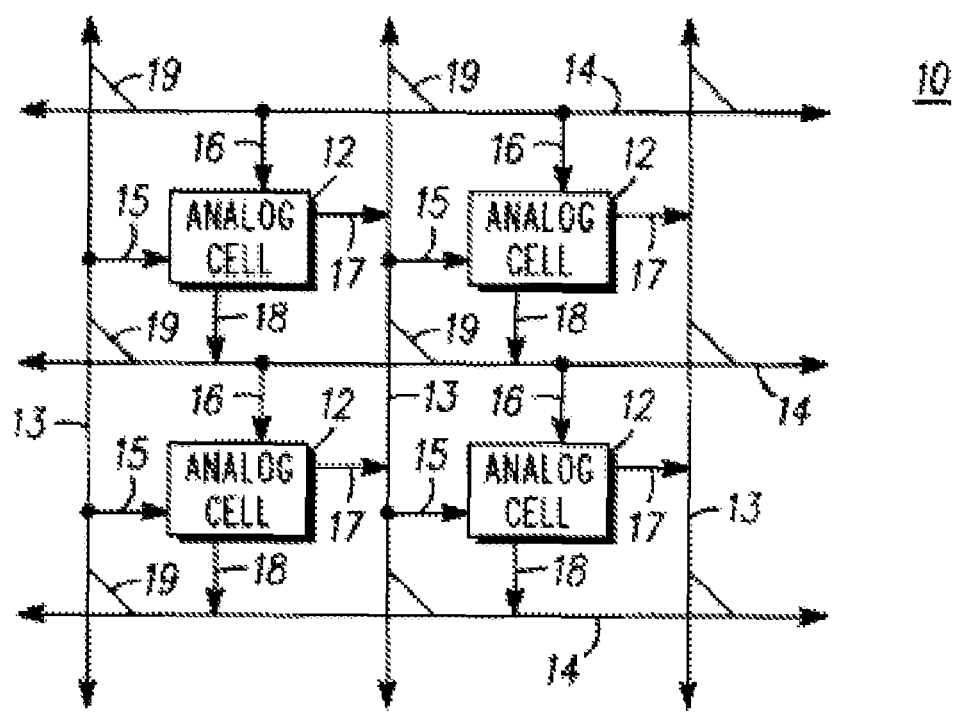
FIG. 1 is a block diagram of a programmable analog nano-array in accordance with the present invention.

FIG. 1 is a block diagram of a programmable array using nano-analog electronics in an integrated circuit configuration. Nano-analog array 10 includes a plurality of programmable analog cells 12 arranged along a plurality of interconnect channels that form a switching network which includes bus lines 13 and 14 for routing analog signals. Input and output signals are transferred between analog cells 12 and buses 13 and 14 by means of analog switching devices such as transmission gates through which analog signals can be transferred with little or no distortion. Control over the switching devices is provided by digital signals that may be stored in a memory such as random access memory (RAM) or read-only memory included in the cell. Alternatively, a centralized memory array can be used to control the switching devices in all of the analog cells 12. As a further alternative, external memory can be used if provision is made for routing the binary control signals to individual analog cells 12. As yet a further alternative, control over the switching devices may be directly provided by other digital circuitry instead of a memory array. Signal routing between bus 13 and bus 14 is provided by switching devices 19.

Figure 2:
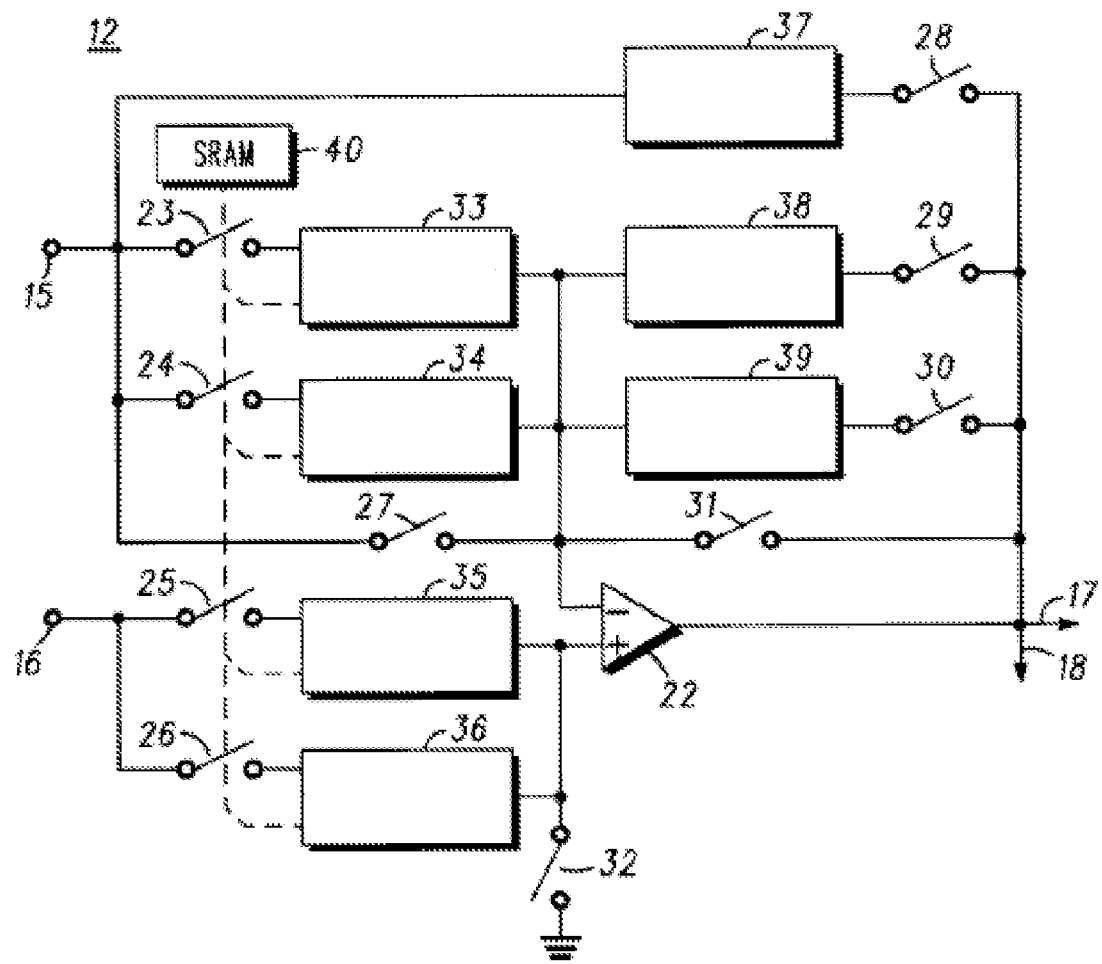
FIG. 2 is a schematic diagram of a first embodiment of a programmable nano-cell in accordance with the present invention.

FIG. 2 is a schematic diagram of a programmable analog cell 12 including an active circuit 22, switches 23-32, programmable nano-elements 33-39, and a static random access memory (SRAM) 40. Input signals are received on input terminals 15 and 16 and output signals are produced on output terminals 17 and 18. Output terminals 17 and 18 are shown as connected together to drive horizontal and vertical conductors 13 and 14. In an alternative embodiment, output terminals 17 and 18 could be isolated such that active circuit 22 drives output terminal 17 and another active circuit included in programmable analog cell 12 drives output terminal 18.

Fabrication of Nano Electronic Components and Systems

As described below, the nano-elements can be formed last in the fabrication sequence in one embodiment. Conventional semiconductor structures are formed as is conventional, which for example includes semiconductor devices produced by photolithography or E-beam lithography. During the next to the last conventional step, gold electrodes are formed. Then a resist layer is formed over the last layer, and selective etching is performed to expose the gold electrodes. A solution containing the nano-elements are spin-coated on top, where the nano-elements self-assemble to form one or more devices such as resistors, capacitors, inductors, antennas, emitters and sensors, among others. Other coating techniques compatible with the present invention include hopper coating, curtain coating. The nano-elements bond to preselected spots on the gold electrodes and self-assemble to form a regular array of resistors, capacitors, inductors, acoustic emitters, acoustic sensors, light emitters, light sensors, among others. In one embodiment, the nano-elements do not need patterning. In another embodiment, patterning of the nano-elements is accomplished by any of the generally available photolithographic techniques utilized in semiconductor processing. However, depending on the particular material chosen, other techniques such as laser ablation or inkjet deposition or electrostatic deposition may also be utilized to pattern the nano-elements. In particular nanoimprint lithography can be used to pattern the nano-elements.

In another embodiment, the substrate may be formed from silicon, gallium arsenide, indium phosphide, and silicon carbide to name a few. Active devices will be formed utilizing conventional semiconductor processing equipment. Other substrate materials can also be utilized, depending on the particular application in which the array will be used. For example various glasses, aluminum oxide and other inorganic dielectrics can be utilized. In addition, metals such as aluminum and tantalum that electrochemically form oxides, such as anodized aluminum or tantalum, can be utilized. Those applications utilizing non-semiconductor substrates, active devices can also be formed on these materials utilizing techniques such as amorphous silicon or polysilicon thin film transistor (TFT) processes or processes used to produce organic or polymer based active devices. Accordingly, the present system is not intended to be limited to those devices fabricated in silicon semiconductor materials, but will include those devices fabricated in one or more of the available semiconductor materials and technologies known in the art.

The process of creating the first layer of electrical conductors may consist of sputter deposition, electron beam evaporation, thermal evaporation, or chemical vapor deposition of either metals or alloys and will depend on the particular material chosen for the electrical conductors. Conductive materials such as polyaniline, polypyrrole, pentacene, thiophene compounds, or conductive inks, may utilize any of the techniques used to create thin organic films. For example, screen printing, spin coating, dip coating, spray coating, ink jet deposition and in some cases, as with PEDOT, thermal evaporation are techniques that may be used.

Depending on the particular memory device being fabricated, the electrical contacts may be created either on a substrate or directly on the semiconducting polymer film. Patterning of the electrical conductors is accomplished by any of the generally available photolithographic techniques utilized in semiconductor processing. However, depending on the particular material chosen, other techniques such as laser ablation or inkjet deposition may also be utilized. In particular one my utilized nanoimprint lithography or techniques for forming nanowires. For additional information on nanoimprint lithography see for example, U.S Application No. 20030230746, the content of which is incorporated by reference. Combinations of different conductive materials may also be utilized that might result in very different processes being utilized. For example it may be desirable to utilize PEDOT as the material for the lower electrical traces and indium tin oxide for the upper electrical traces if erasure via light is desired. Another embodiment may use a typical metal such as tantalum, tungsten, or even highly doped polysilicon for electrical conductors deposited on the substrate and an organic conductor such as PEDOT for electrical conductors deposited on the semiconducting polymer film. The process of creating a third layer of electrical conductors on a second semiconducting polymer film, for the applications utilizing such a layer, can be the same or similar to that used for the first layer, depending on whether the electrical conductor is the same as that used for the first layer electrical conductors. The process of creating a semiconducting polymer film will depend on the particular binder and organic dopant chosen. The particular binder and organic dopant chosen will depend, for example, on the particular electronic properties desired, the environment in which the device will be used, and whether a thin dielectric film will be utilized. Depending on the particular binder chosen the appropriate solvents are utilized that provide sufficient solubility for both the binder and the organic dopant as well as providing appropriate viscosity for the particular coating or casting process chosen. An exemplary process for creating a semiconducting polymer layer uses HPLC grade tetrahydrofuran as a solvent to dissolve the binder bisphenol-A-polycarbonate and a mono-substituted diphenylhydrazone compound (DPH) in appropriate concentrations to obtain the desired electrical properties. If a substrate is utilized, the composition and properties of the substrate are also taken into consideration, in order to obtain good adhesion between the substrate and the semiconductor polymer layer, as well as the electrical conductors and the semiconductor polymer layer. Adhesion promoters or surface modification may also be utilized. In addition, a planarizing layer may also be utilized, for example, when electrical conductors are formed on rather than in the substrate. The process of creating a multilayer semiconductor polymer film, for those applications utilizing such a structure, can be the same or similar as the process used to create the first layer, depending on whether the binder or organic dopant is the same as that used for the first layer. The process of forming a dielectric thin film, will depend on the particular material chosen, and may consist of, for example, sputter deposition, chemical vapor deposition, spin coating, or electrochemical oxidation. For example, tantalum electrical conductors may be deposited using conventional sputtering or electron beam deposition techniques. After the tantalum is deposited a thin tantalum oxide layer may be formed electrochemically. This process may be performed prior to or after photolithographic processing to define the electrical conductors. Another embodiment may utilized a thin silicon oxide layer deposited on the electrical conductors or on the semiconducting polymer film depending on which electrical conductor is chosen to have the thin dielectric film. A thin silicon oxide film may be deposited by any of a wide range of techniques, such as sputter deposition, chemical vapor deposition, or spin coating of a spin on glass material, to name a few. Still another embodiment may utilize a thin non-conducting polymer layer, such as the binder polymer, deposited on the appropriate electrical conductors. Other embodiments may utilize self assembled monolayers or silane coupling agents to produce a thin dielectric film. The process of creating a second or multilayer dielectric thin film, for those applications utilizing such a structure, can be the same or similar as the process used to create the first layer, depending on whether the thin dielectric film is the same as that used for the first layer. The process of creating the second layer of electrical conductors will depend, for example, on the particular binder and organic materials chosen as well as the presence or absence of the thin dielectric film and its chemical composition. For example, a polyimide binder will typically sustain higher temperatures than a polyethylene binder will. Thus, thermal or electron beam deposition of tungsten or platinum electrical conductors may be used on a polyimide binder whereas chemical vapor deposition, spin coating or thermal evaporation of an organic conductor may be desirable for a polyethylene binder. The particular deposition process utilized will also depend on the degree of defects generated in either the thin dielectric film if used or the semiconducting polymer film. In addition, the particular process as well as the process parameters will also be chosen to optimize adhesion between the film or films to which the electrical conductor material is deposited on. The process of creating a fourth layer of electrical conductors, for those applications utilizing such a structure, can be the same or similar as the processes used to create the first through third layers, depending on whether the fourth layer is the same as that used for the first layer. A passivation layer can be used to protect the semiconducting polymer film from damage and environmental degradation when appropriate. For example, a passivation layer providing a barrier to oxygen permeation can be desirable when utilizing a memory device having an acceptor organic dopant or functional group because oxygen is a potential electron trap. In addition, depending on the particular organic dopant and electrical conductors utilized it may also be desirable to utilize a passivation layer providing a moisture barrier to reduce corrosion. Further depending on whether active devices are present an electrostatically dissipating or shielding film may also be desirable.

Due to the nano-structure, the absolute capacitance values of programmable nano-elements 33-39 are well controlled using self-assembly processes. Additional degree of matching accuracy can be attained if programmable elements 33-39 are carefully laid out on the die. Such matching accuracy results in a given binary control chemical structure producing substantially equal capacitances when applied to each of the programmable elements 33-39. For this reason, operations of active circuit 22 can be controlled using ratios of programmable resistance, capacitance, or inductance whenever possible. For example, in one embodiment where the nano-elements 33-39 are capacitors, if it is desired to operate amplifier 22 with a closed loop gain of 35/32, a binary control chemical structure "35" is applied to control programmable capacitor 39 and a binary control chemical structure "32" is applied to control programmable capacitor 33. The resulting capacitance ratio is 35/32.

Active circuit 22 is shown as an amplifier having inverting and non-inverting inputs and an output. Analog cell 12 can also include comparators and other types of active circuits, and can include more than one active circuits of the same type. For example, a single cell can incorporate several amplifiers controlled by programmable nano-elements 33-39 that act as capacitors to operate as an active filter. Active circuit 22 typically includes an output buffer stage (not shown) for driving the capacitances and the load capacitances of terminals 17 and 18.

SRAM 40 comprises memory storage for controlling the operation of switches 23-32 and switches included in programmable capacitors 33-39. To simplify the figure, such control is indicated by the dotted line from SRAM 40 to switches 23-26 and programmable capacitors 33-36. Switches 23-26 and programmable capacitors 33-36 can alternatively be controlled by other types of memory, such as read only memory, or with combinational logic.

It should be noted that programmable analog cell 12 can alternatively be implemented with programmable nano-elements that include passive elements other than switchable capacitors, such as programmable nano-resistors or programmable nano-inductors.

Dynamically Reconfigurable Logic-Analog Devices

In one embodiment, a field programmable array includes a matrix of configurable logic and/or analog blocks embedded in a programmable routing mesh. Each configurable logic/analog block (CLAB) can provide one or more of the functions provided by an AND gate, flip-flop, latch, inverter, NOR gate, exclusive OR gate, resistor, capacitor, inductor, LED, light sensor, as well as combinations of these functions to form more complex functions. The particular function performed by the CLAB is determined by control signals that are applied to the CLAB from a control logic circuit. The control logic circuit is formed integrally with, and as part of, the integrated circuit on which the CLAB is formed. If desired, control information can be stored and/or generated outside of this integrated circuit and transmitted to the CLAB. The actual set of control bits provided to each CLAB on the integrated circuit depends upon the functions that the CLAB and, more globally, the integrated circuit are to perform. Each CLAB typically has a plurality of input and output pins, and a set of programmable interconnect points (PIPs) for each input and output pin. The general interconnect structure of the field programmable array includes a plurality of interconnect segments and a plurality of PIPs, wherein each interconnect segment is connected to one or more other interconnect segments by programming an associated PIP. A field programmable array also includes an access PIP that either connects an interconnect segment to an input pin or an output pin of the CLAB. Because the PIPs are programmable, any given output pin of a CLAB is connectable to any given input pin of any other desired CLB. Thus, a specific field programmable array configuration having a desired function is created by selected generation of control signals to configure the specific function of each CLAB, together with selected generation of control signals to configure the various PIPs that interconnect the CLABs. Each PIP typically includes a switch such as a single pass transistor. The state of conduction, i.e. whether the switch is opened or closed, is controlled by application of the control signals discussed above to a transistor control terminal, e.g. a gate. The state of the control signal stored in a latch determines whether a pass transistor (PIP) is turned on or off, thereby opening or closing a path in the field programmable interconnect, as described in U.S. Pat. No. 5,581,198, the contents of which is incorporated by reference. In various embodiments, single molecule magnet (SMM) cells or single molecule optical storage cells as described in this application are used to implement PIPs to increase number of PIPs that can be fit onto an integrated circuit. In one embodiment, the SMMs replace RAMs coupled to switches or pass transistors as described in the '198 patent. In another embodiment, the SMMs operate both as storage and switch, namely that as programmed, the SMMs are positioned in predetermined positions that link various interconnected segments to program the field programmable array. In yet another embodiment, the PIP can be a nanobridge. The nanobridge includes a thin layer of copper sulfide that separates a copper electrode from a titanium electrode. The copper whisker is grown and dissolved across a metal-copper sulphide-metal sandwich. When a sufficient voltage is applied, copper ions migrate up through the copper sulfide dielectric, forming a nanoscale whisker that eventually connects the two electrodes part of the interconnect structure described above. Applying a programming voltage to the nanobridge structure causes a low-resistance conduction path to form through a dielectric material, shorting together two electrodes. Applying a reverse bias causes the ions to migrate away from the titanium, in effect taking down the bridge. In one embodiment, the nano-bridge is used as a dynamically reconfigurable device where programming voltages are used to establish links between elements of the reconfigurable device. Alternatively, a solid, silver atomic-laden chalcogenide electrolyte can be used as the sandwiched layer with silver being deposited on the electrode to form the bridge when in the on-state.

Alternatively, in place of SMMs, electric field activated switches can be used. For example, United States Patent Application 20020114557 provides a molecular system for nanometer-scale reversible electronic and optical switches, specifically, electric field-activated molecular switches that have an electric field induced band gap change that occurs via a molecular conformation change or a tautomerization. Changing of extended conjugation via chemical bonding change to change the band gap is accomplished by providing the molecular system with one rotating portion (rotor) and two or more stationary portions (stators), between which the rotor is attached. The molecular system of the present invention has three branches (first, second, and third branches) with one end of each branch connected to a junction unit to form a "Y" configuration. The first and second branches are on one side of the junction unit and the third branch is on the opposite side of the junction unit. The first branch contains a first stator unit in its backbone, the junction unit comprises a second stator unit, and the first branch further contains a rotor unit in its backbone between the first stator unit and the second stator unit. The second branch includes an insulating supporting group in its backbone for providing a length of the second branch substantially equal to that of the first branch, wherein the rotor unit rotates between two states as a function of an externally-applied field. In other embodiments, a molecule called a rotaxane or a catenane trapped between two metal electrodes can be switched from an ON state to an OFF state by the application of a positive bias across the molecule. The ON and OFF states differed in resistivity by about a factor of 100 and 5, respectively, for the rotaxane and catenane.

In one embodiment, the nano-elements include nano-bridge. The nanobridge includes a thin layer of copper sulfide that separates a copper electrode from a titanium electrode. The copper whisker is grown and dissolved across a metal-copper sulphide-metal sandwich. When a sufficient voltage is applied, copper ions migrate up through the copper sulfide dielectric, forming a nanoscale whisker that eventually connects the two electrodes. Applying a programming voltage between the two electrodes in the nanobridge structure causes a low-resistance conduction path to form through a dielectric material, shorting together two electrodes. Applying a reverse bias voltage between the two electrodes causes the ions to migrate away from the titanium, in effect taking down the bridge, that is, the configuration of the nanobridge structure is removed. In one embodiment, the nano-bridge is used as a dynamically reconfigurable device where programming voltages are used to establish links between elements of the reconfigurable device. Applications include Field Programmable Gate Array (FPGA). The semiconductor elements in the first layer or the spin-coated nano-elements in the second layer form a Field Programmable Gate Array. At least one of the semiconductor elements in the first layer or the nano-elements are reconfigurable.

Alternatively, a solid, silver atomic-laden chalcogenide electrolyte can be used as the sandwiched layer with silver being deposited on the electrode to form the bridge when in the on-state.

Figure 3:
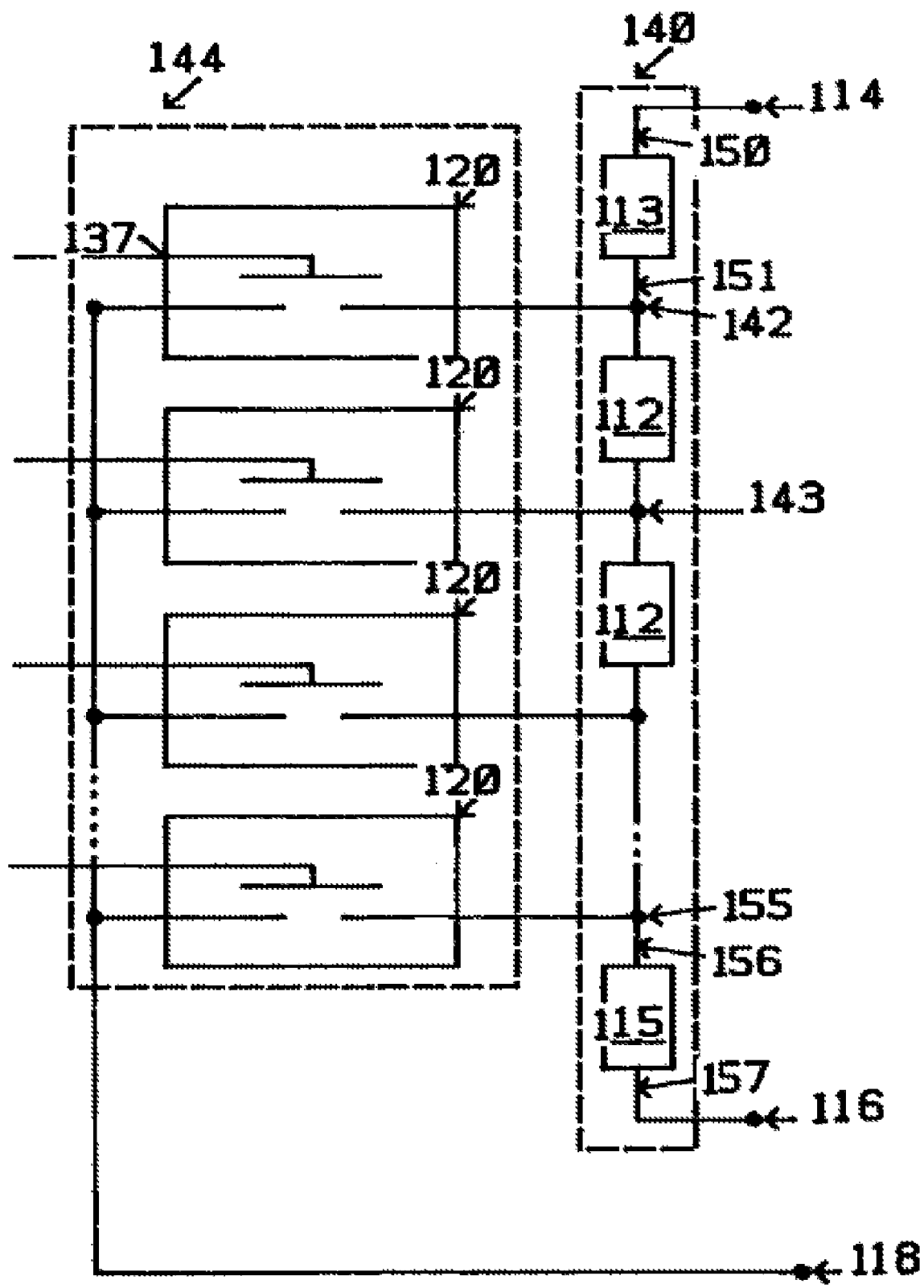
FIG. 3 is a schematic diagram of a second embodiment of a programmable nano-cell in accordance with the present invention.

FIG. 3 shows another embodiment having a series chain of molecular or nano-elements 140 and a means for accessing the chain. In the embodiment shown in FIG. 3, the nano-elements 140 are resistors. The series chain 140 has a plurality of two terminal molecular elements connected in series. The series chain 140 has a first element 113, a last element 115, and one or more intermediate molecular elements 112. Each of the intermediate molecular elements 112 is connected to the molecular element adjacent to it at a node, of which node 143 is typical. One terminal 150 of the first molecular element is connected to a first terminal 114. The other terminal 151 of the first molecular element 113 is connected to the first intermediate molecular element at node 142. Similarly, the last molecular element 115 has one of its terminals 156 connected to the adjacent intermediate molecular element at node 155. The other terminal 157 of the last element 115 is connected by the accessing means to a second terminal 116. At least one of the terminals 150 and 157 is accessible to an external circuit connected to the apparatus of the present invention. The accessing means connects a selected one of the nodes to a third terminal 118.

In one embodiment, the nano-elements are resistors. Other embodiments, however, in which the nano-elements are capacitors, inductors, or a combination of one or more of these three types of molecular elements or nano-elements will be obvious to those skilled in the art. In one version, each of the molecular elements provides the same impedance (for the resistor embodiment), capacitance (for the capacitor embodiment), or inductance (for the inductor embodiment). Embodiments in which the molecular elements are of different values will also be obvious to those skilled in the art.

In the resistor embodiment, each element in the series chain 140 has a series combination of two resistive elements. In one embodiment, the first such element is chosen to have a positive temperature coefficient, and the second such element is chosen to have a negative temperature coefficient. The temperature coefficients in question are selected such that the series or parallel combination of the two elements is a resistive element having an essentially zero temperature coefficient.

A switch 144 is provided for connecting a selected node to the terminal 118. The switch 144 in turn includes a selector (not shown) to select which node is to be connected, and a memory device (not shown) for storing the identity of the selected node connected to the third terminal 118 and for causing the node to be reconnected to the third terminal 118 when power is reapplied or restored to the apparatus.

The switch 144 has a plurality of electrically controllable switches, one tied to each node in the chain 140 of which switch 120 is typical. The switch 120 can be a transistor fabricated in accordance with semiconductor technique or a nano-transistor as discussed in this case. One terminal of each electrically controllable switch is connected to a respective one of the nodes. The other terminal of each switch is connected in common with all other corresponding switch terminals to the third terminal 118. Each electrically controllable switch may be closed by applying a signal to a control terminal of which terminal 137 is typical. When an electrically controllable switch is closed, the node to which it is connected is connected to the third terminal 118. Only one of the electrically controllable switches is closed at a given time. In the preferred embodiment, each electrically controllable switch is a conventional MOSFET.

A selecting means can be a binary shift register in which all of the bits are set to "0" except for one bit which contains a "1" could also be used. Each bit in the shift register would be connected to a corresponding electrically controllable switch control terminal. In this embodiment, the choice of which node is connected to the third terminal 118 would be made by shifting the contents of the register either up or down by signals on appropriate control lines. The state of the shift register could be stored in an electrically reprogrammable memory which has one bit corresponding to each of the bits in the shift register.

In another embodiment, the nano-elements are transistors or diode. As discussed in US Patent Publication 20030178617, the disclosure of which is incorporated hereof by reference, a self-aligned carbon-nano tube field effect transistor semiconductor device is fabricated. The device comprises a carbon-nano tube deposited on a substrate, a source and a drain formed at a first end and a second end of the carbon-nano tube, respectively, and a gate formed substantially over a portion of the carbon-nano tube, separated from the carbon-nano tube by a dielectric film. Alternatively, a carbon-nano tube field effect transistor semiconductor device is provided. The device comprises a vertical carbon-nano tube wrapped in a dielectric material, a source and a drain formed on a first side and a second side of the carbon-nano tube, respectively, a bilayer nitride complex through which a band strap of each of the source and the drain is formed connecting the carbon-nano tube wrapped in the dielectric material to the source and the drain, and a gate formed substantially over a portion of the carbon-nano tube.

In accordance with another embodiment of the present invention, the nano-elements such as transistors, capacitors, inductors and diodes, can be provided using DNA molecules as a support structure. DNA binding proteins are used to mask regions of the DNA as a material, such as a metal is coated onto the DNA. The present invention also provides methods of making integrated circuits using DNA molecules as a support structure. Methods for making DNA based transistors, capacitors, inductors and diodes are discussed in US Patent Publication 20010044114, the disclosure of which is incorporated hereof by reference.

In one embodiment, the nano-elements can be a substantially two-dimensional array made up of single-walled nano tubes aggregating (e.g., by van der Waals forces) in substantially parallel orientation to form a monolayer extending in directions substantially perpendicular to the orientation of the individual nano tubes. Such monolayer arrays can be formed by conventional techniques employing "self-assembled monolayers" (SAM) or Langmiur-Blodgett films. nano tubes are bound to a substrate having a reactive coating (e.g., gold). Typically, SAMs are created on a substrate which can be a metal (such as gold, mercury or ITO (indium-tin-oxide)). The molecules of interest, here the SWNT molecules, are linked (usually covalently) to the substrate through a linker moiety. The linker moiety may be bound first to the substrate layer or first to single-wall nano tubes ("SWNT") molecule (at an open or closed end) to provide for reactive self-assembly. Langmiur-Blodgett films are formed at the interface between two phases, e.g., a hydrocarbon (e.g., benzene or toluene) and water. Orientation in the film is achieved by employing molecules or linkers that have hydrophilic and lipophilic moieties at opposite ends.

In one embodiment the SAM, or two-dimensional monolayer, described above may be the starting template for preparing a three dimensional self-assembling structures. Where the end caps of the component SWNT molecules have monofunctional derivatives the three-dimensional structure will tend to assemble in linear head-to-tail fashion. By employing multi-functional derivatives or multiple derivatives at separate locations it is possible to create both symmetrical and non symmetrical structures that are truly three-dimensional.

Carbon nano tubes in material obtained according to the foregoing methods may be modified by ionically or covalently bonding functionally-specific agents (FSAs) to the nano tube. The FSAs may be attached at any point or set of points on the fullerene molecule. The FSA enables self-assembly of groups of nano tubes into geometric structures. The groups may contain tubes of differing lengths and use different FSAs. Self-assembly can also occur as a result of van der waals attractions between derivitized or underivitized or a combination of derivitized and underivitized fullerene molecules. The bond selectivity of FSAs allow selected nano tubes of a particular size or kind to assemble together and inhibit the assembling of unselected nano tubes that may also be present. Thus, in one embodiment, the choice of FSA may be according to tube length. Further, these FSAs can allow the assembling of two or more carbon nano tubes in a specific orientation with respect to each other.

By using FSAs on the carbon nano tubes and/or derivitized carbon nano tubes to control the orientation and sizes of nano tubes which are assembled together, a specific three-dimensional structure can be built up from the nano tube units. The control provided by the FSAs over the three-dimensional geometry of the self assembled nano tube structure can allow the synthesis of unique three-dimensional nano tube materials having useful mechanical, electrical, chemical and optical properties. The properties are selectively determined by the FSA and the interaction of and among FSAs.

Properties of the self-assembled structure can also be affected by chemical or physical alteration of the structure after assembly or by mechanical, chemical, electrical, optical, and/or biological treatment of the self-assembled fullerene structure. For example, other molecules can be ionically or covalently attached to the fullerene structure or FSAs could be removed after assembly or the structure could be rearranged by, for example, biological or optical treatment. Such alterations and/or modifications could alter or enable electrical, mechanical, electromagnetic or chemical function of the structure, or the structure's communication or interaction with other devices and structures.

In yet another embodiment, a nanotube wired OR logic can be implemented. The upper nanotubes or nanowires IN0, IN1, IN2, IN3 contact lower nanotube, thus forming a plurality of low resistance PN-type junctions discussed in US Application Serial No. 20030200521, the content is incorporated by reference. Alternatively, a programmable diode OR array with nanotubes can be used. The OR devices do not produce gain. Therefore, restoring logic performing signal restoration is needed to provide gain, either at the microscale or at the nanoscale level. Signal restoration allows high signals to be driven higher and low signals to be driven lower, in order to allow an arbitrary number of devices to be cascaded together and a logical distinction between a low logical value and a high logical value to be maintained. Therefore, signal restoration helps protecting the circuit against noise and allows arbitrary circuit composition. Restoring logic is provided at the nanoscale level in order to allow the output of a first stage to be used as input for a second stage, making it possible to compute through an arbitrary number of logic stages without routing the signal to non-nanoscale (e.g., microscale) wires. Using the FET junctions, NMOS-like inverters, NAND, AND, NOR, or OR logic can be built. In a first scenario (pull-up), all inputs IN0, . . . , INM−1 of the FETs are low. As a consequence, there is conduction through all the FETs formed at the wire crossings (no evacuation of charge). Since there is conduction through all the FETs and the top end of the series of FETs is connected to a power supply driven to a high voltage, the wire can be pulled up to the high voltage of the power supply. The output is now high. In a second scenario (pull-down), one of the inputs IN0, . . . , INM-1 is high. Ideally, there is no conduction through the portion of the wire under this FET. This breaks the path from the high voltage supply to the output region of the wire. In absence of current flow, the output cannot be pulled up to the high voltage. The static pulldown is always weakly enabled. If it is not pulling against a strong connection to the high voltage supply, as in the previous scenario, the weak static pulldown will be able to pull the output down to a low voltage level. The output of the FET is now low. Alternatively, restoration at the nanoscale level could also be obtained by means of precharge logic structures. In the simplest case, the static pull-down in the NOR is replaced with a precharge gate. Alternatively, the single pull-down line could be microscale instead of nanoscale. Additionally, an additional microscale input to disable the pull-up could be added. Operation is started by driving the new pull-up line (the additional input) to a high value (disabling current flow to the power supply), and enabling the pull-down precharge line by driving it to a low value. This will allow the output to charge to a low value. After the output is charged to a low value, the pull-down is disabled. The output will remain at the low value for which it is now precharged. Subsequent to this, the new pull-up line is enabled. If all of the inputs are low, conduction is allowed to the power supply and the output can be pulled up. If one or more of the inputs are high, there is no such path and the output remains at a low voltage level. Thus, the device continues to perform its NOR function. Alternate stages will use complementary precharge phases, in order not to release the pull-up enable line while the inputs to a stage are still precharging and have not been allowed to evaluate.

Nano Antenna

Examples of useful electric properties of the above described self-assembled geometric structure include: operation as an electrical circuit, a specific conductivity tensor, a specific response to electromagnetic radiation, a diode junction, a 3-terminal memory device that provides controllable flow of current, a capacitor forming a memory element, a capacitor, an inductor, a pass element, or a switch.

The geometric structure may also have electromagnetic properties that include converting electromagnetic energy to electrical current, an antenna, an array of antennae, an array that produces coherent interference of electromagnetic waves to disperse those of different wavelength, an array that selectively modifies the propagation of electromagnetic waves, or an element that interacts with optical fiber.

Figure 4:
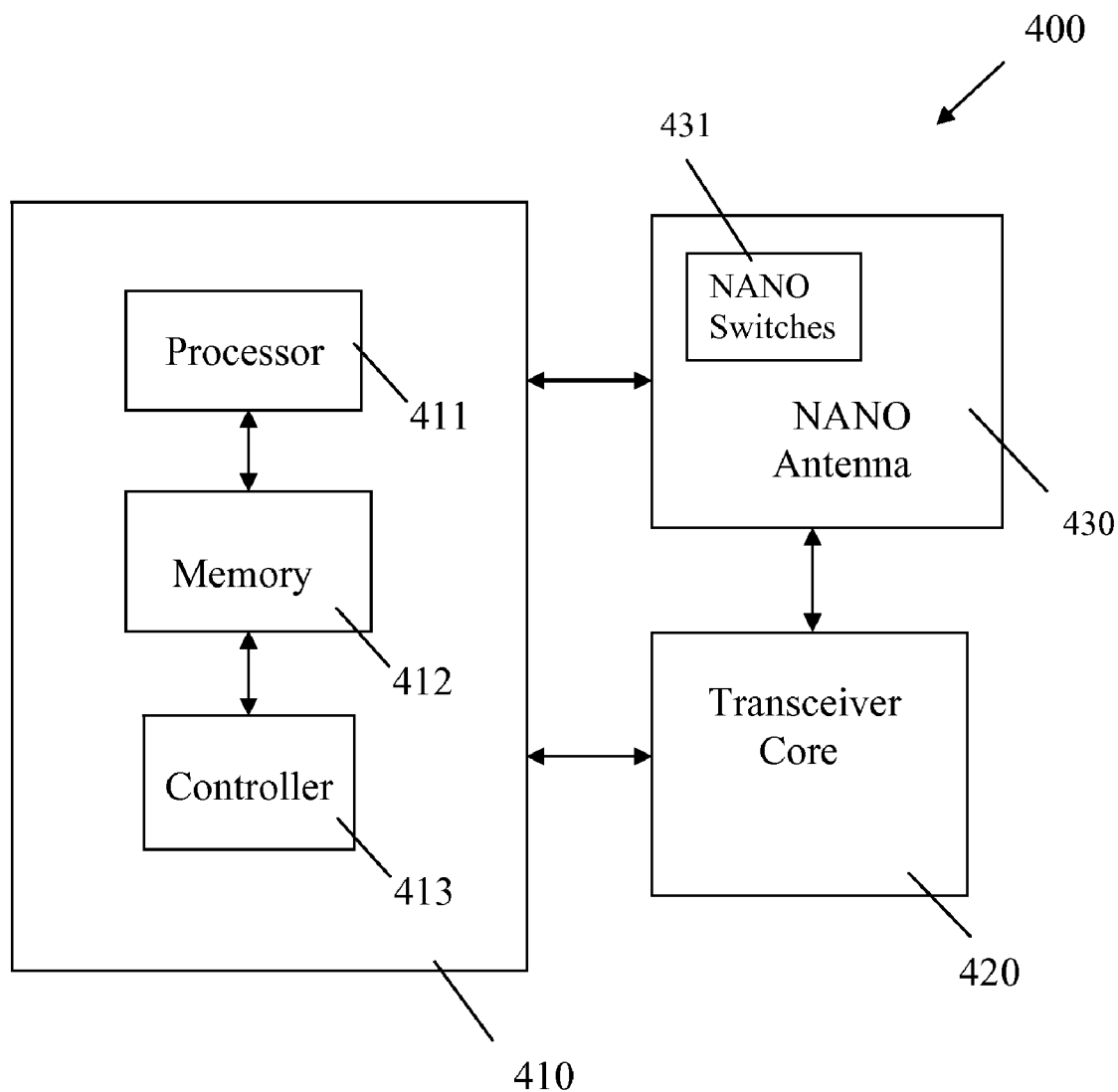
FIG. 4 is a block diagram of a wireless communication device comprising nano antenna in accordance with the present invention.

In the present invention, such antenna is referred as nano antenna. A wireless communication device 400 including such an nano antenna 430 is shown in FIG. 4. The wireless communication device 400 include a processor core 410 that is fabricated using conventional semiconductor processes such as CMOS. The processor 411 can include one or more central processor units (CPUs), one or more digital signal processors (DSPs), and Application Specific Integrated Circuits (ASICs). The memories 412 can include dynamic random access memory (DRAM), Read Only memory (ROM), and flash memory. The controller 413 controls the transceiver 420 and the nano antenna 430 to enable it to transmit and receive wireless signals at different frequencies.

The processor core 410 can be fabricated using nano elements such as transistors, diodes, capacitors, resistors, as described above or using conventional semiconductor processes on a semiconductor substrate.

In accordance with the present invention, the electromagnetic properties of the nano 440 antenna can be selectively determined by the FSA and the interaction of and among FSAs. For example, the lengths, location, and orientation of the molecules can be determined by FSAs so that an electro-magnetic field in the vicinity of the molecules induces electrical currents with some known phase relationship within two or more molecules. The spatial, angular and frequency distribution of the electromagnetic field determines the response of the currents within the molecules. The currents induced within the molecules bear a phase relationship determined by the geometry of the array. In addition, application of the FSAs could be used to facilitate interaction between individual tubes or groups of tubes and other entities, which interaction provides any form of communication of stress, strain, electrical signals, electrical currents, or electromagnetic interaction. This interaction provides an "interface" between the self-assembled nano structure and other known useful devices.

Choice of FSAs can also enable self-assembly of compositions whose geometry imparts useful chemical or electrochemical properties including operation as a catalyst for chemical or electrochemical reactions, sorption of specific chemicals, or resistance to attack by specific chemicals, energy storage or resistance to corrosion.

Examples of biological properties of FSA self-assembled geometric compositions include operation as a catalyst for biochemical reactions; sorption or reaction site specific biological chemicals, agents or structures; service as a pharmaceutical or therapeutic substance; interaction with living tissue or lack of interaction with living tissue; or as an agent for enabling any form of growth of biological systems as an agent for interaction with electrical, chemical, physical or optical functions of any known biological systems.

FSA assembled geometric structures can also have useful mechanical properties which include but are not limited to a high elastic to modulus weight ratio or a specific elastic stress tensor. Optical properties of geometric structures can include a specific optical absorption spectrum, a specific optical transmission spectrum, a specific optical reflection characteristic, or a capability for modifying the polarization of light.

Self-assembled structures, or fullerene molecules, alone or in cooperation with one another (the collective set of alternatives will be referred to as "molecule/structure") can be used to create devices with useful properties. For example, the molecule/structure can be attached by physical, chemical, electrostatic, or magnetic means to another structure causing a communication of information by physical, chemical, electrical, optical or biological means between the molecule/structure and other structure to which the molecule/structure is attached or between entities in the vicinity of the molecule/structure. Examples include, but are not limited to, physical communication via magnetic interaction, chemical communication via action of electrolytes or transmission of chemical agents through a solution, electrical communication via transfer of electronic charge, optical communication via interaction with and passage of any form with biological agents between the molecule/structure and another entity with which those agents interact.

Fullerene nano tubes can be used to replace the more traditional conductive elements of an antenna. For example, an (n,n) tube in conjunction with other materials can be used to form a Schottky barrier which would act as a light harvesting antenna. In one embodiment, a (10,10) tube can be connected via sulfur linkages to gold at one end of the tube and lithium at the other end of the tube forming a natural Schottky barrier. Current is generated through photo conductivity. As the (10, 10) tube acts like an antenna, it pumps electrons into one electrode, but back flow of electrons is prevented by the intrinsic rectifying diode nature of the nano tube/metal contact.

In forming an antenna, the length of the nano tube can be varied to achieve any desired resultant electrical length. The length of the molecule is chosen so that the current flowing within the molecule interacts with an electromagnetic field within the vicinity of the molecule, transferring energy from that electromagnetic field to electrical current in the molecule to energy in the electromagnetic field. This electrical length can be chosen to maximize the current induced in the antenna circuit for any desired frequency range. Or, the electrical length of an antenna element can be chosen to maximize the voltage in the antenna circuit for a desired frequency range. Additionally, a compromise between maximum current and maximum voltage can be designed. A Fullerene nano tube antenna can also serve as the load for a circuit. The current to the antenna can be varied to produce desired electric and magnetic fields. The length of the nano tube can be varied to provide desired propagation characteristics. Also, the diameter of the antenna elements can be varied by combining strands of nano tubes. Further, these individual nano tube antenna elements can be combined to form an antenna array. The lengths, location, and orientation of the molecules are chosen so that electrical currents within two or more of the molecules act coherently with some known phase relationship, producing or altering an electromagnetic field in the vicinity of the molecules. This coherent interaction of the currents within the molecules acts to define, alter, control, or select the spatial, angular and frequency distributions of the electromagnetic field intensity produced by the action of these currents flowing in the molecules. In another embodiment, the currents induced within the molecules bear a phase relationship determined by the geometry of the array, and these currents themselves produce a secondary electromagnetic field, which is radiated from the array, having a spatial, angular and frequency distribution that is determined by the geometry of the array and its elements. One method of forming antenna arrays is the self-assembly monolayer techniques discussed above.

In another embodiment of the present invention, nano wires can be formed to provide the resonant circuit in the nano antenna 430. The orientation of the nano wires can be controlled to maximize the reception signal strengths of the wireless communication device 400. Methods of orienting nanowires include the use of mask based processes alone or in combination with flow based alignment of the nanowires to provide oriented and positioned nanowires on surfaces. The populations of nanowires can also be controlled. Details of the control of nanowire orientation and population are discussed in US Patent Publication 20030186522, the disclosure of which is incorporated hereof by reference.

In accordance with the present invention, a plurality of equivalent nano circuits at different orientations are provided in the nano antenna 430. The orientation of the nano circuits are disposed such that wireless signals can be received at high strength at any orientation of the wireless communication device 400 relative to the field propagation direction of the incoming wireless wave.

In another embodiment, a plurality of nano tubes can be connected by nano switches 431 in a serial circuit to provide the nano antenna 430. The electrical lengths of the circuit and thus the resonant frequencies can be configured by turning on and off different combinations of the nano switches 431, depending on the required frequencies of various telecommunication protocols. Communications standards and protocols supported by the processor core 410, the transceiver core 420, and nano antenna 430 include for example Global System for Mobile Communications (GSM), General Packet Radio Service (GPRS), Bluetooth, IEEE802.11 etc.

Fullerene molecules can be used to replace traditional electrically conducting elements. Thus fullerene molecules or self-assembled fullerene groups can be the basis of electrical circuits in which the molecule transfers electrical charge between functional elements of the circuit which alter or control the flow of that charge or objects in which the flow of electrical current within the object performs some useful function such as the redistribution of the electric field around the object or the electric contact in a switch or a response of the object to electromagnetic waves. As an example, nano tubes can also be self-assembled to form a bridge circuit to provide full wave rectification. This device can include four nano tubes, each forming an edge of a square, and four buckyballs, one buckyball would be located at each corner of the square. The buckyballs and nano tubes can be derivitized to include functionally specific agents. The functionally specific agents form linkages connecting the buckyballs to the nano tubes and imparting the required geometry of the bridge. A fullerene diode can be constructed through the self-assembly techniques described above. The diode can be composed of two bucky tubes and a bucky capsule. The bucky capsule can also be derivitized to form a zwiterrion. For example, the bucky capsule can include two positive groups, such as the triethyl amine cation and two negative groups, such as $CO_2$-anion. In one embodiment, each end of the bucky capsule is connected to a (10, 10) bucky tube by a disulfide bridge. Thus, sulfur serves as the functionally-specific agent.

Various molecules or nano-elements can be coupled to one or more electrodes in a layer of an IC substrate using standard methods well known to those of skill in the art. The coupling can be a direct attachment of the molecule to the electrode, or an indirect attachment (e.g. via a linker). The attachment can be a covalent linkage, an ionic linkage, a linkage driven by hydrogen bonding or can involve no actual chemical attachment, but simply a juxtaposition of the electrode to the molecule. In some preferred embodiments, a "linker" is used to attach the molecule(s) to the electrode. The linker can be electrically conductive or it can be short enough that electrons can pass directly or indirectly between the electrode and a molecule of the storage medium. The manner of linking a wide variety of compounds to various surfaces is well known and is amply illustrated in the literature. Means of coupling the molecules will be recognized by those of skill in the art. The linkage of the storage medium to a surface can be covalent, or by ionic or other non-covalent interactions. The surface and/or the molecule(s) may be specifically derivatized to provide convenient linking groups (e.g. sulfur, hydroxyl, amino, etc.). In one embodiment, the molecules or nano-elements self-assemble on the desired electrode. Thus, for example, where the working electrode is gold, molecules bearing thiol groups or bearing linkers having thiol groups will self-assemble on the gold surface. Where there is more than one gold electrode, the molecules can be drawn to the desired surface by placing an appropriate (e.g. attractive) charge on the electrode to which they are to be attached and/or placing a "repellant" charge on the electrode that is not to be so coupled.

Nano Memory Devices

Figure 5:
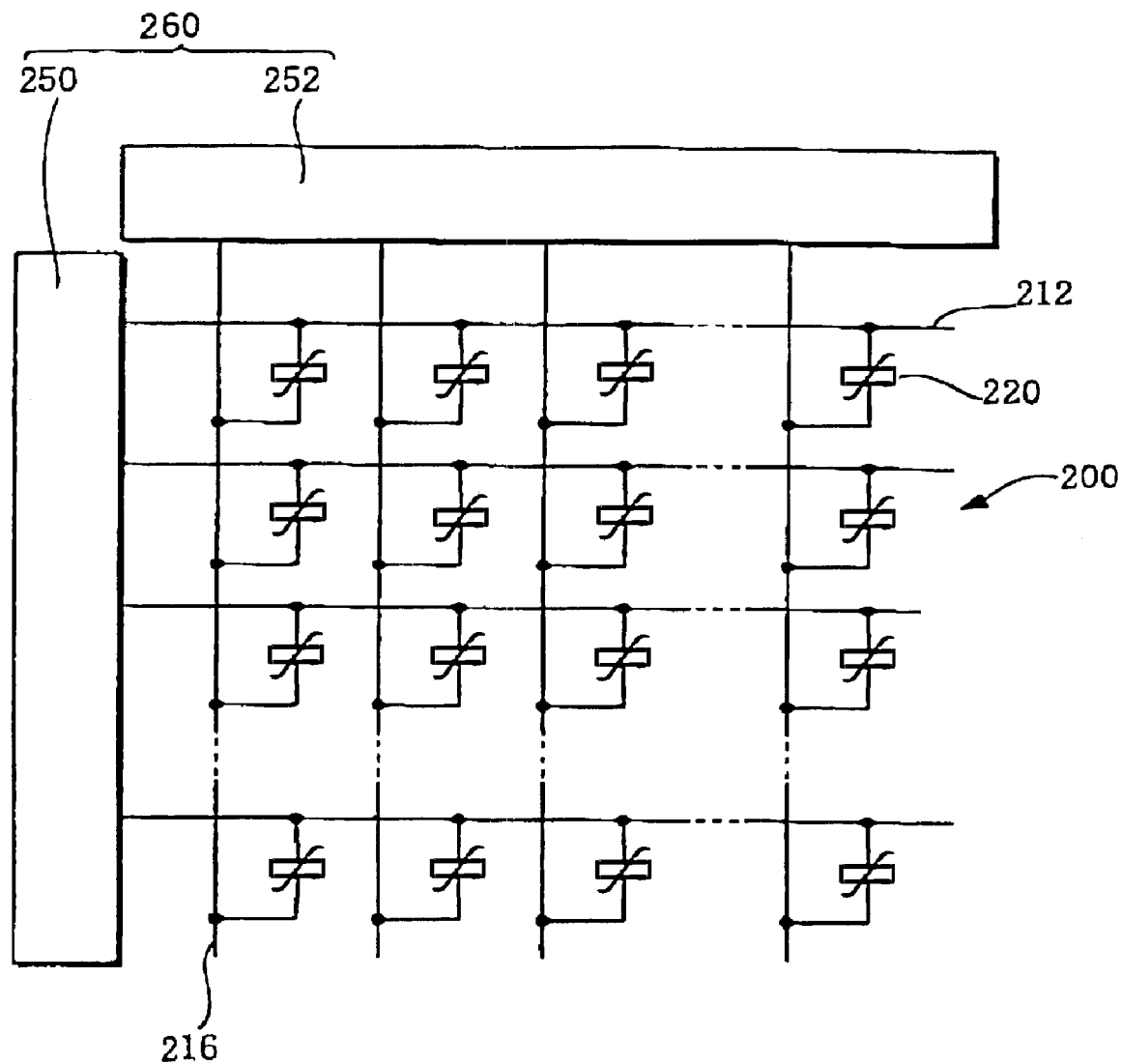
FIG. 5 is a schematic diagram of the architecture of memory devices comprising nano elements in accordance with the present invention.

In yet another embodiment shown in FIG. 5, the nano-elements can be an array of single-molecule magnets (SMMs). In one embodiment, arrays of SMMs can be used in combination with semiconductor structures to replace solid state memory systems or alternatively the SMMs can be deposited on a disk platter to achieve high density disk drive. The SMM molecules can be used for spin-based molecular electronics devices as well.

Single molecule magnets (SMMs) are nano magnets that consist of a core of strongly exchange-coupled transition metal ions with a large magnetic moment per molecule. SMM form crystals that are monodisperse—every molecule in a crystal has the same spin, orientation, magnetic anisotropy and atomic structure. Hence magnetic measurements of a crystal can be used to characterize the properties of individual magnetic molecules. SMMs have magnetic anisotropy that favors the magnetic moment to be either up or down with respect to the easy axis. The energy barrier between up and down states (the anisotropy barrier) leads to magnetic hysteresis and to magnetic bistability for magnetic data storage. Transitions between up and down magnetic states can occur by thermal activation and quantum tunneling. Due to the discrete energy spectrum, transitions are favored when up and down energy levels are in resonance, or, more precisely, have an anticrossing. These resonances only occur at certain magnetic fields. Each SMM has a fixed molecular size and shape, and unlike normal magnets, the properties of the SMM are due to intrinsic molecular properties. The SMM gains its properties from the large potential energy barrier between the spin "up" and spin "down" states. One exemplary SMM is $Mn_{12}O_{12}(O_2CMe)_{16}(H_2O).2MeCO_2H.4H_2O$, with $S=10$, and its related Mn complexes. Other classes of in the Mn family of molecules, $Mn_4O_3$ complexes, can also be used as SMMs.

The SMMs are made from transition metal clusters exhibiting magnetic bistability. The SMMs possess a high-spin ground state (S), which, when combined with a negative axial zero-field splitting (D<0), leads to an energy barrier for spin reversal. The SMMs incorporate oxo-based bridging ligands that mediate the magnetic exchange coupling between metal centers. In another embodiment having clusters with larger spin reversal barriers, cluster systems formed by replacing $Cr^{III}$ with $Mo^{III}$ in the linear cluster $[(Me_3tacn)_2$-(cyclam) $NiCr_2(CN)_6]_2+(Me_3tacn)N,N',N''$-trimethyl-1,4,7-triazacyclononane; cyclam=1,4,8,11-tetraazacyclotetradecane) or an analogous substitution in the trigonal prismatic cluster $[(Me_3tacn)_6MnCr_6(CN)_{18}]^{2+,3c}$ bearing a higher spin ground state of $S=3/2$ can be used as a cyano-bridged single-molecule magnet.

As shown in FIG. 5, an SMM memory device includes a memory cell array 200 constructed over a substrate such as the substrate includes a silicon-on-insulator (SOI) wafer. In the memory cell array 200, first signal electrodes (chemical structure lines or word lines) 212 for selecting rows and second signal electrodes (bit lines) 216 for selecting columns are arranged to intersect at right angles. The first signal electrodes may be the bit lines and the second signal electrodes may be the chemical structure lines, differing from this example. An SMM layer 214 is disposed at least between the first signal electrodes 212 and the second signal electrodes 216. Therefore, memory cells 220, each of which includes an SMM, are formed at intersections between the first signal electrodes 212 and the second signal electrodes 216. A peripheral circuit section 260 including a peripheral driver circuit for selectively allowing information to be written into or read from the memory cells and an amplifier circuit which for reading the information is also formed. The peripheral circuit section 260 includes a first driver circuit 250 for selectively controlling the first signal electrodes 212, a second driver circuit 252 for selectively controlling the second signal electrodes 216, and a signal detecting circuit (not shown) such as a sense amplifier, for example.

As specific examples of the peripheral circuit section 260, a Y gate, a sense amplifier, an input-output buffer, an X address decoder, a Y address decoder, and an address buffer can be given. A write line is formed near the SMM cell 220 and the write line is used for writing and inverting magnetization of nano-magnetic material layer of the SMM cell 220 by a current flow, as the magnetization is magnetic information.

The peripheral circuit section 260 may be formed by MOS transistors formed on a substrate (single crystal silicon substrate, for example). In the case where the substrate is formed of a single crystal silicon substrate, the peripheral circuit section 260 can be integrated on the same substrate as the memory cell array 200. The SMMs are formed last by spin-coating a solution containing self-assembled SMMs on a wafer after the wafer has been processed and devices are formed using conventional semiconductor fabrication techniques. Conventional semiconductor structures are formed as is conventional. During the next to the last conventional step, gold electrodes are formed. Then a resist layer is formed over the last layer, and selective etching is performed to expose the gold electrodes. A solution containing the SMMs is spin-coated on top, where the SMMs self-assemble.

Writing to the bit is accomplished by applying a polarized voltage pulse through a nanocircuit element. A positive pulse will pull the SMM and a negative pulse will push the SMM. The bistable nature of the bit will result in the SMM staying in the positioned end when the pulse is removed since that is where the energy is lowest. To read the bit, another nanocircuit element is biased with a VREAD voltage. If the SMM is present in the detection end, it supplies the necessary energy levels for current to resonantly tunnel across the junction to the ground voltage (in a fashion analogous to a resonant tunneling diode) resulting in a first stable state being read. If the SMM is not present in the detection end, the energy levels are shifted out of resonance and the current does not tunnel across the junction and a second stable state is read. Other forms of read/write structure (e.g., microactuators) can be employed as will be recognized by one skilled in the art.

A memory device can be constructed using either a two- or three-dimensional array of the SMMs. Because the SMMs are molecular in size, a dense memory chip can be fabricated. Further, the wiring width and the area of each cell is reduced. The switching electric field can be reduced by using the SMM memory cell and write current necessary for writing a magnetization invert may be reduced, whereby power consumption being restrained and switching being carried out at high speed. The nano coercive force is small and the switching magnetic field is small. When the nano-device is used as a memory cell of a magnetic memory, the current of a write wiring for generating a magnetic field necessary for inverting magnetization can be reduced. Therefore, according to the magnetic memory forming the memory cell by nano-magnets, a highly integrated formation can be performed, the power consumption is reduced, and the switching speed can be made faster.

The molecular memory such as SMM memory is used as on-chip data or off-chip storage device for a processor chip. In one embodiment, the memory system organization is a multi-level memory hierarchy. A combination of a small, low-latency level one (L1) memory backed by a higher capacity, yet slower, L2 memory and finally by main memory provides the best tradeoff between optimizing hit time and miss time. Different molecular memory arrays with differing speed and size requirements can be deployed in a computer system. For example, a high speed static RAM can be used as L1 memory, while a high speed high density nano memory array can be used as L2 memory and low speed nano memory array can be used as regular memory. In one system on a chip, processor logic and cache is implemented using traditional semiconductor structure, and a large main memory array is provided on chip using molecular memory. Finally, nano-head disk drive can be used as long term data storage devices.

Nano Disk Drive

Figure 6A:
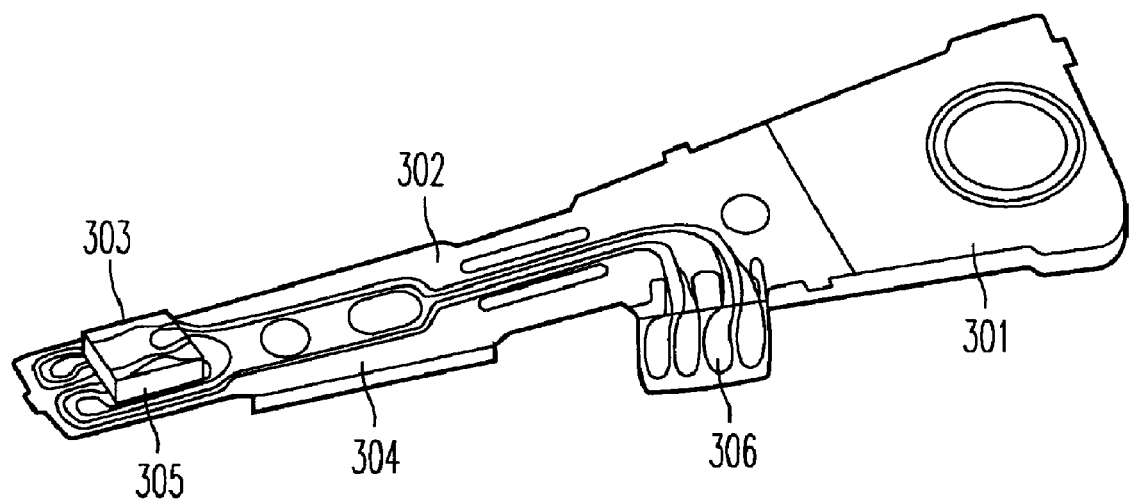
FIGS. 6A-6B show perspective views of an exemplary single molecule magnet data storage device, in this case a disk drive in accordance with the present invention.

Yet another embodiment is an embodiment in which the SMMs are applied to a magnetic head. FIG. 6A is a perspective view of a nano-magnetic head assembly mounted with an SMM head. An actuator arm 301 is provided with a hole for being fixed to a fixed shaft inside of a magnetic disk apparatus and is provided with a bobbin portion for holding a drive coil (not illustrated) and the like. A suspension 302 is fixed to one end of the actuator 301. A front end of the suspension 302 is wired with a lead wire 304 for writing and reading signals, one end of the lead wire 304 is coupled with respective electrode of a nano-magnetic head 305 mounted on a head slider 303, and the other end of the lead wire 304 is connected to an electrode pad 306. The nano-head 305 is fabricated using thin-film type substrate, with spin-coating of the SMM elements at the last stages of head manufacture.

The nano-head 305 has one or more nano sub-heads so that it can access information serially or in parallel for improved data throughput. In addition, error correction codes can be encoded and decoded on the nano-head. Further, each of the sub-heads can be part of a RAID array. The nano-head 305 provides data used for standard RAID levels including 1, 3, and 5 or combinations of two other RAID levels. For example, in RAID 1+0 (also called RAID 10), multiple RAID 1 pairs are striped for faster access; and in RAID 15, two RAID 5 arrays are mirrored for added reliability.

Figure 6B:
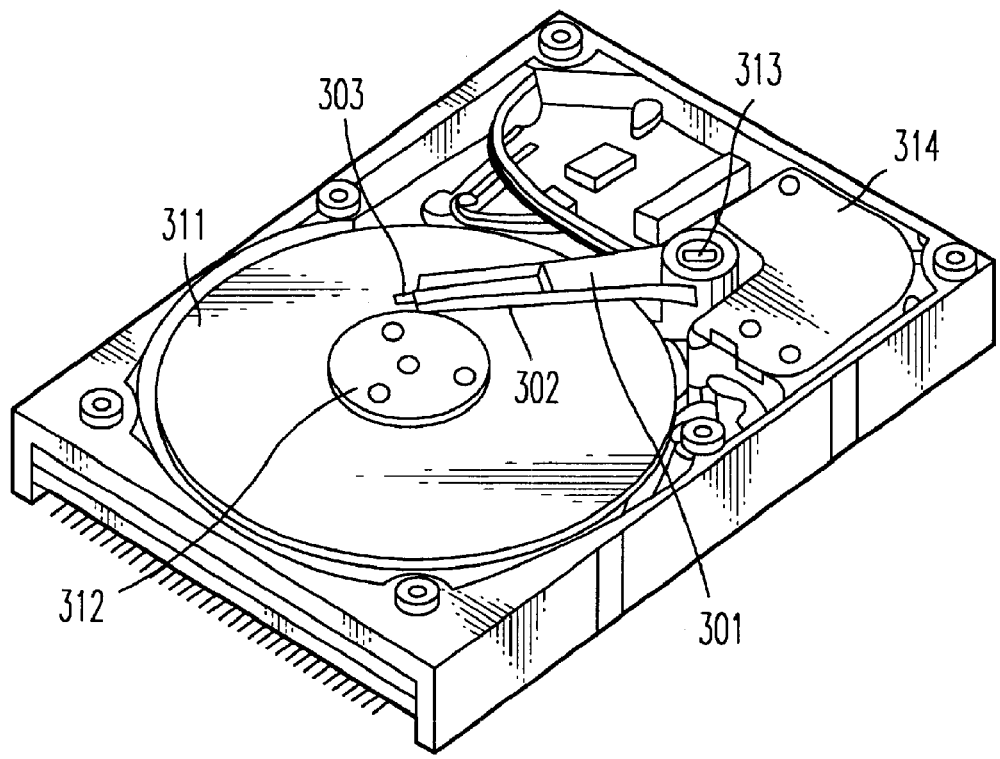

FIG. 6B is a perspective view of an inner structure of a magnetic disk apparatus (magnetic information reproducing apparatus) mounted with the magnetic head assembly of FIG. 6A. A nano-magnetic disk 311 is mounted on a spindle 312 and is rotated by a motor (not illustrated) responding to a control signal from a control portion of a drive apparatus (not illustrated). The nano-magnetic disk 311 has a surface that is processed using thin film deposition with a spin-coat of the self-assembled SMMs late in fabrication of the disk 311. The actuator arm 301 is fixed to a fixed shaft 313 for supporting the suspension 302 and the head slider 303 at the front end thereof. When the magnetic disk 311 is rotated, a surface of the head slider 303 opposed to the disk 311 is held in a floating state from a surface of the magnetic disk 311 by a predetermined amount, thereby reproducing the magnetic information of the magnetic disk. At another end of the actuator arm 301, a chemical coil motor 314 is provided and includes a type of a linear motor. The chemical coil motor 314 includes a drive coil (not illustrated) wound up to the bobbin portion of the actuator arm 301 and a magnetic circuit including a permanent magnet and an opposed yoke arranged to be opposed to each other to interpose the coil. The actuator arm 301 is supported by ball bearings (not illustrated) provided at two upper and lower locations of the fixed shaft 313 and can freely be slidingly rotated by the chemical coil motor 314.

Nano-Optical Dram

In yet another embodiment, the nano-elements can be an array of optical storage molecules (OSMs). In one embodiment, arrays of OSMs can be used in combination with semiconductor structures to replace solid state memory systems or alternatively the OSMs can be deposited on a disk platter to achieve high density disk drive. The OSM molecules can be used for spin-based molecular electronics devices as well.

The OSMs convert energy patterns into electronic digital signals by exposing an image plate having OSMs supported by a matrix to an energy pattern. The energy pattern can be provided by a plurality of optical signals output from a bundle of optical fibers of optical circuitry. The applications include telecommunication and parallel optical computing. A plurality of energy patterns recorded by the array of OSMs in electronic signals can be considered as snapshots of optical signals which can be read as optical signals or electronic signals.

In one embodiment, the OSM can be a nanophase storage luminescence material of the general formula X/Y, wherein X is at least one guest and Y is a host. The host can be selected from the group consisting of organic, inorganic, glass, crystalline, non-crystalline, porous materials or combinations thereof. The host can be semiconducting nanoparticles such as insulating nanoparticles, conducting nanoparticles, and combinations thereof. The semiconductor nanoparticle can be sulfide, telluride, selenide, or oxide semiconductors. The semiconductor nanoparticle is selected from the group of $Zn_xS_y$, $Zn_xSe_y$, $Zn_xTe_y$, $Cd_xS_y$, $Cd_xSe_y$, $Cd_xTe_y$, $Pb_xS_y$, $Pb_xSe_y$, $Pb_xTe_y$, $Mg_xS_y$, $Ca_xS_y$, $Ba_xS_y$, and $Sr_xS_y$, wherein $0 \leq x \leq 1$, $0 \leq y \leq 1$. The semiconductor nanoparticle can be ZnS. The semiconductor nanoparticle can also be represented by the general formula $(M_{1-z}N_z)_xA_{1-y}B_y$, wherein M=Zn, Cd, Pb, Ca, Ba, Sr, Mg; N=Zn, Cd, Pb, Ca, Ba, Sr, Mg; A=S, Se, Te, O; B=S, Se, Te, O; $0 \leq x \leq 1$, $0 \leq y \leq 1$, $0 \leq z \leq 1$). The semiconductor nanoparticle can also be $Zn_{0.4}Cd_{0.4}S$.

The writing of optical signals involves the conversion of optical signals to electronic states via photon induced electronic excitations. As discussed in Application Serial No. 20030064532, nano particle energy structure can be modified via quantum size confinement. When electrons and holes are produced in nano particles by excitation, the electrons and holes may de-excite or relax to the lowest excited states and recombine to give luminescence. They also may be trapped by electron or hole traps at the surfaces, interfaces, or/and in the surrounding matrix. The electrons or holes at traps are in a metastable state.

The read-out of the recorded electronic data converted from optical signals can be achieved by several mechanisms. 1) When stimulated by light or by heat some electrons or holes may be released and go back to the nano particles, recombining to provide luminescence—i.e., photostimulated luminescence (PSL) or thermoluminescence. Light energy is provided to optically stimulate the photostimulated luminescence nano particles. The nano particles release the stored energy and provide luminescence due to electron-hole recombination; and converting the luminescence into digital signals indicative of the energy pattern. The stimulating light or heat energies can be applied uniformly to the array of OSMs and detecting the PSL and thermoluminescence by a 2D optical sensor. 2) Alternatively, the recombination and luminescence of the stored electrons and holes in the energy pattern can also be stimulated by sweeping electric voltage pulses along the word lines and bit lines. The detection of the stimulated luminescence signals include only a single or 1D array of optical detectors. 3) Finally, the stored electrons and holes from the exposed energy pattern can be read out electronically as in conventional memory devices using the electronic circuitry in the memory cell array as described below. Transistors can be provided to convert the stored charge to voltage signals. Additional conductive lines connecting to the collector, the emitters, the gates can be provided to facilitate the readouts. The invention device is similar to electrically erasable programmable read-only memory (EEPROM) devices with additional optical writing (via 2D optical pattern) capabilities.

An exemplified architecture of the OSM memory device is illustrated in FIG. 5. The OSM memory device includes a memory cell array constructed over a substrate and the substrate includes a silicon-on-insulator (SOI) wafer. In the memory cell array, first signal electrodes (word lines) for selecting rows and second signal electrodes (bit lines) for selecting columns are arranged to intersect at right angles. The first signal electrodes may be the bit lines and the second signal electrodes may be the chemical structure lines, differing from this example. An OSM layer is disposed at least between the first signal electrodes and the second signal electrodes. Therefore, memory cells, each of which includes an OSM, are formed at intersections between the first signal electrodes and the second signal electrodes. A peripheral circuit section (including a peripheral driver circuit for selectively allowing information to be written into or read from the memory cells) and an amplifier circuit which for reading the information is also formed. The peripheral circuit section includes a first driver circuit for selectively controlling the first signal electrodes, a second driver circuit 252 for selectively controlling the second signal electrodes, and a signal detecting circuit such as a sense amplifier, for example.

The OSMs are formed last by spin-coating a solution containing self-assembled OSMs on a wafer after the wafer has been processed and devices are formed using conventional semiconductor fabrication techniques. Conventional semiconductor structures are formed as is conventional. During the next to the last conventional step, gold electrodes are formed. Then a resist layer is formed over the last layer, and selective etching is performed to expose the gold electrodes. A solution containing the OSMs are spin-coated on top, where the OSMs self-assemble. Writing to the bit is accomplished by applying a tightly focused light emitter that can be a nanocircuit element. To read the bit, another nanocircuit element such as a light detector detects whether the optical DRAM cell is on or off based on the stored light energy. If the OSM is on, it supplies the necessary energy levels for current to resonantly tunnel across the junction to the ground voltage (in a fashion analogous to a resonant tunneling diode) resulting in a first stable state being read. If the OSM is off, the energy levels are shifted out of resonance and the current does not tunnel across the junction and a second stable state is read. Other forms of read/write structure (e.g., microactuators) can be employed as will be recognized by one skilled in the art.

A memory device can be constructed using either a two- or three-dimensional array of the OSMs. Because the OSMs are molecular in size, a dense memory chip can be fabricated. Further, the wiring width and the area of each cell is reduced. The switching light field can be reduced by using the OSM memory cell and write current necessary for writing an optical invert may be reduced, whereby power consumption being restrained and switching being carried out at high speed. The molecular memory such as OSM memory is used as on-chip data or off-chip storage device for a processor chip. In one embodiment, the memory system organization is a multi-level memory hierarchy. A combination of a small, low-latency level one (L1) memory backed by a higher capacity, yet slower, L2 memory and finally by main memory provides the best tradeoff between optimizing hit time and miss time. Different molecular memory arrays with differing speed and size requirements can be deployed in a computer system. For example, a high speed static RAM can be used as L1 memory, while a high speed high density nano optical DRAM array can be used as L2 memory and low speed nano memory array can be used as regular memory. In one system on a chip, processor logic and cache is implemented using traditional semiconductor structure, and a large main memory array is provided on chip using molecular memory. Finally, nano-head disk drive can be used as long term data storage devices.

Nano Optical Interconnect

In a high speed multi-chip module (MCM) environment, chip-to-chip connections are usually made using bond wires, with microstrip lines on the MCM substrate used to interconnect chips that are farther apart. Presently, electrical bond wires are used to interconnect microchips. Using the electrical wires has serious drawbacks. The electrical wires are sensitive to electromagnetic interference and themselves create such interference which poses especially serious problems for distribution of timing signals. The electrical wires must be located at the edges of chips. Signal attenuation and phase delay depend upon the length of the electrical wires. Thus, depending on the lengths of the electrical wires and their locations in the module, it may be difficult to achieve equal attenuation and/or equal signal phase delay among multiple wires, if needed. In addition, in many cases signal bandwidths of several Gigahertz are desirable but cannot be achieved if electrical wires are used because electrical bond wires act as open antennae at high frequencies and introduce noise coupling among the wires. For example, bond wires of 500 micrometers in length and 1 mil (0.001 inch) diameter carrying 10 milliamperes of current will produce appreciable (100 millivolts or more) coupling or cross-talk at 10 Gigahertz even when they are spaced several pitch distances apart, a typical pitch being 100 to 150 micrometers. This effect will substantially limit the maximum speed of a typical MCM module having hundreds of bond wires from several chips. The cross-talk is even more severe when the chips are located farther apart and require longer bond wires. Previously, optoelectronic devices such as vertical-cavity lasers and photodetectors have been bonded onto microelectronic chips to provide free-space optical interconnections. However, such lasers and detectors are bulky.

In one embodiment of the invention, nano optical elements such as OSMs are used with an optical waveguide to interconnect MCMs to provide an optical interconnection system. In one embodiment, conventional electronics are deposited using standard semiconductor processing techniques. Next, OSMs and light detectors are spin-coated above the semiconductor layer and they self assemble to form transmitters or receivers at designated locations on the MCMs. During fabrication, the MCMs are immersed in a solution that allows nano-optical interconnect (nano-lightpath) to self-assemble in 3D space between the transmitters and the receivers. The self-assembly is keyed so that specific nano-lightpaths bond between specific transmitter and receiver pairs. One type of keying uses chemical bond key encoding or DNA encoding. The nano light fibers or other suitable light conductors to interconnect the OSMs to their respective light detectors. Lightpaths traverse several physical links but information traveling on a lightpath is carried optically from end-to-end. The system is insensitive to electromagnetic interference; needs not be located at the edges of a chip but rather can be placed for optimal utility to the circuit function; can be given the same or other pre-specified lengths regardless of the placement in the module; and are capable of high signal bandwidths without causing the cross-talk problem. The optical interconnection system can further include a semiconductor region over or in the substrate. An electronic circuit can be formed conventional semiconductor techniques. The electronic circuit controls or monitors the interconnection of the optical signals.

In another embodiment for wide area networking, the system performs wavelength routing, which is a form of circuit switching. In wavelength-routed networks, a lightpath, which is an end-to-end optical communication connection, is established before data can be sent. Such lightpaths are called "wavelength-routed" because each uses a dedicated wavelength channel on every link along a physical path, and hence, once data is transmitted on a specific wavelength by its source, how the data will be routed (or switched) at the intermediate nodes will be determined by the "color" of the wavelength only. Optical packet switching (OPS) is similar to traditional electronic packet switching, except for that payload (i.e., data) will remain in optics, while its header may be processed electronically or optically. In one embodiment, the above optical random access memory performs optical buffering. Optical burst switching (OBS) is a technique for transmitting bursts of traffic through an optical transport network by setting up a connection and reserving resources end to end for the duration of a burst. OBS is a way to achieve a balance between the coarse-grained wavelength routing and fine-grained optical packet switching.

In another embodiment, the system includes a nano-optical switch is a nano photonic switch having N full-duplex ports, each of which can connect to any other without OEO conversion, although the switch may still be controlled by electronic signals. Broadly speaking, switches refer to devices that may be called add-drop multiplexers (ADMs), routers, and cross-connects. An add/drop multiplexer (ADM) is an optical system that is used to modify the flow of traffic through a fiber at a routing node. An ADM passes traffic on certain wavelengths through without interruption or opto-electronic conversions, while other wavelengths are added or dropped, carrying traffic originating or terminating at the node. A wavelength router (WR) is a more powerful system than an ADM. For each of the wavelengths it takes in a signal at an input port and routes it to a particular output port, independent of the other wavelengths. A WR with N input and N output ports capable of handling k wavelengths can be considered as k independent NXN single wavelength switches. These switches have to be preceded by a wavelength demultiplexer and followed by a wavelength multiplexer to implement a WR. They are sometimes also called wavelength routing switches (WRS) or wavelength crossconnects (WXCs). Equipped with WCs, a WXC becomes a wavelength interchanging switch, also known as wavelength interchanging crossconnect (WIXC). (Note that a wavelength crossconnect (WXC) is commonly called an optical crossconnect (OXC).

In a wavelength-routed network embodiment, nano-wavelength crossconnect (WXC) or nano-optical crossconnect (OXC) nodes are inter-connected by nano-fiber links. A lightpath is realized by allocating a wavelength on each link on the path between the two nodes. Each link can support a certain number of wavelengths. To avoid wavelength continuity constraint, nano-wavelength converters (WCs) are used in the network. A wavelength converter is a device that takes in data at one wavelength and outputs it on a different wavelength. Wavelength conversion can play a significant role in improving the utilization of the available wavelength in the network, or reducing the blocking rate for light path requests. The light paths can be set up and taken down upon demand. These are analogous to setting up and taking down circuits in circuit-switched networks. The key elements in the network are the optical crossconnects (OXCs). The major components required to realize OXCs are passive wavelength multiplexers and demultiplexers, switches, and/or wavelength converters. Depending on the functionality available at the nodes, these networks can be classified as either static or reconfigurable. A static network does not have any switches or dynamic wavelength converters in it. A reconfigurable network, on the other hand, contains switches and/or dynamic wavelength converters. The main difference between the two types of networks is that the set of lightpaths that can be established between users is fixed for a static network, whereas it can be changed, by changing the states of the switches or wavelength converters at the OXC nodes, for a reconfigurable network.

Nano Optical Storage Device

In another embodiment, single molecule light sensors are used to provide data storage. The nano-elements convert energy patterns into digital signals by exposing an image plate having a nano particle array supported by a matrix to an energy pattern. The nano particle array formed of photo-stimulated luminescence nano particles which cooperate to store energy indicative of the energy pattern. As discussed in Application Serial No. 20030064532, nano particle energy structure can be modified via quantum size confinement. When electrons and holes are produced in nano particles by excitation, the electrons and holes may de-excite or relax to the lowest excited states and recombine to give luminescence. They also may be trapped by electron or hole traps at the surfaces, interfaces, or/and in the surrounding matrix. The electrons or holes at traps are in a metastable state.

When stimulated by light or by heat some electrons or holes may be released and go back to the nano particles, recombining to provide luminescence—i.e., photostimulated luminescence (PSL) or thermoluminescence. Light energy is provided to optically stimulate the photostimulated luminescence nano particles. The nano particles release the stored energy and provide luminescence due to electron-hole recombination; and converting the luminescence into digital signals indicative of the energy pattern. As a data storage device, the writing light can be either ultra-violet (UV) or blue or any other light having energy higher than the energy gap of the host materials (i.e. the writing light is variable and will depend on the energy gap of the host material). The reading light can be visible or infrared (IR) light, the choice of reading light is also variable and depends on the trap depth of the host material. Semiconductors such as MgS, CaS, SrS, and SrSe doped with rare earth elements such as Ce, Sm, and Eu have been previously considered for optical storage and dosimetric applications. The configuration of the optical writer and optical reader are similar a CD-R or DVD-R drive and similar to the configurations in FIGS. 6A and 6B. The layer of nano particles can be spin-coated over a substrate surface.

Nano Chemical Sensors

Figure 7:
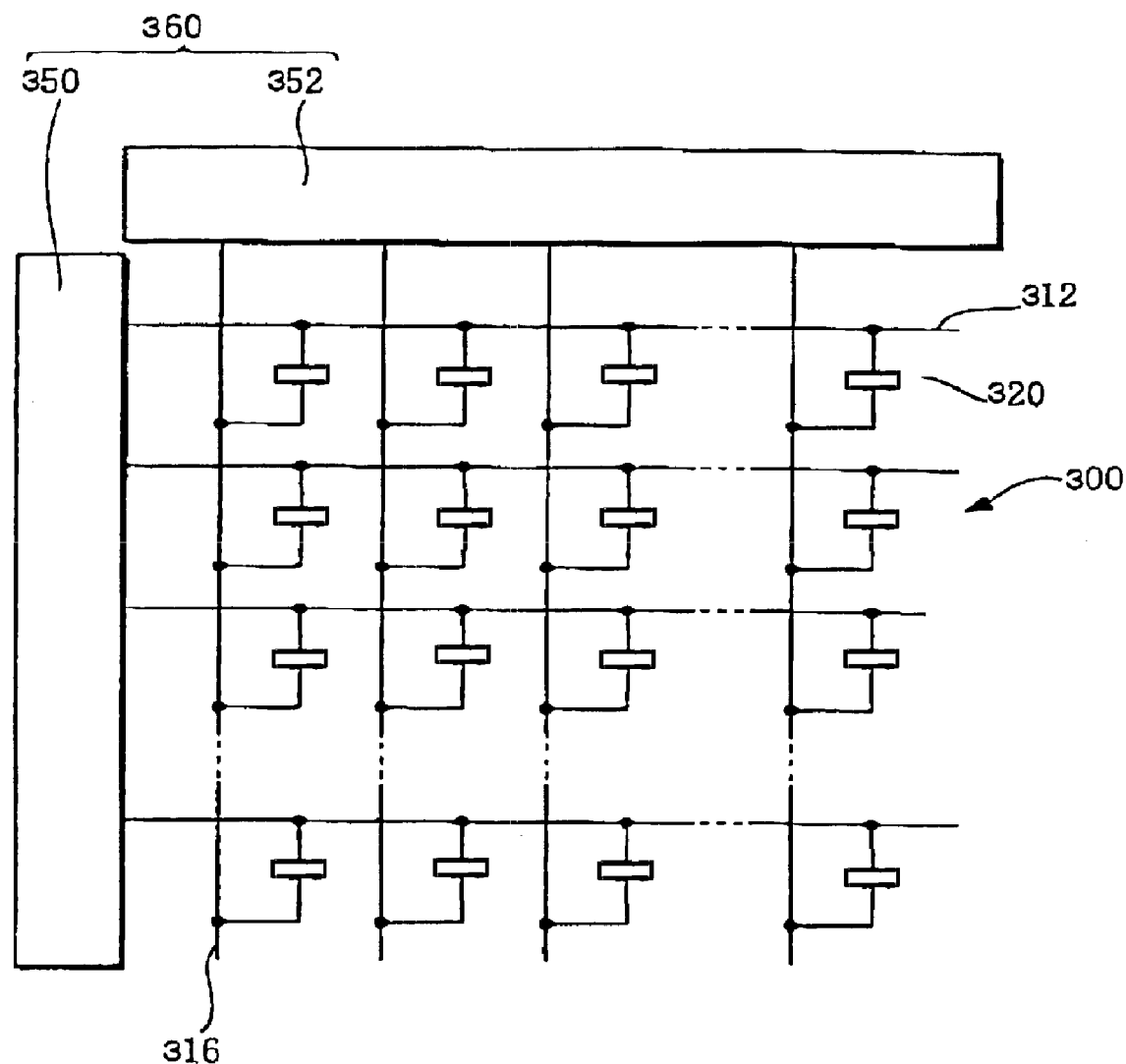
FIG. 7 is a diagram of a system having an array of nano-based chemical and biological sensors in accordance with the present invention.

FIG. 7 is an exemplary diagram of a system having an array of nano-based sensors. The nano-elements can be used as sensors such as Guided-Optics Intrinsic Chemical Sensors. These sensor types are based on the fact that chemical species can affect the waveguide properties. Hence, it is not the absorption or emission properties of an analyte that are measured, but rather the effect of the analyte upon the optical properties of the optical waveguide. More specifically, these sensors are based on one or more of the following effects of the analyte: (a) An increase in the strain/stress of the coating, (b) Modification of the waveguide temperature, (c) Attenuation of the guided light amplitude, (d) Change of the effective refractive index of the mode, (e) Modification of the polarization of the light.

In one embodiment, a sensor includes resonant nano particles embedded in a semipermeable matrix. The nano scale sensor can operate with a single molecule to recognize the presence of a specific short sequence in a mixture of solid molecules, gaseous molecules or aqueous molecules such as DNA or RNA molecules. The system selectively detects and identifies a plurality of chemical species by using an array of nano sensors. When a target molecule binds to the probes (nano particles) in the sensor, the probe molecule changes shape and alters the reflectivity of the sensor. In one embodiment, the nano particles are embedded in a carrier or matrix. The matrix is preferably transparent to an optical sampling wavelength and not Raman active at the Stokes shifts of interest. The optical sample wavelength may be any suitable laser wavelength. The matrix may be any suitable inorganic or polymeric material such as mesoporous silica. The optical sampling geometry can be as a layer deposited onto a reflective substrate exposed to incident light. Alternatively, the optical sampling geometry can be as a cladding layer in a waveguide structure, where the Raman excitation is a result of the evanescent wave of the guided optical mode propagating in that structure.

The analytes of interest are exposed to the semipermeable layer, diffuse through this layer and are adsorbed onto the surfaces of the embedded nano particles. The scattered light is modulated by the Stokes modes of the analyte molecules, and detection consists of spectral analysis of the scattered light using a standard dispersive geometry and lock-in based photodetection. The nano particles' resonances are tuned to match a pump laser wavelength. The nano particles can be functionalized with molecules that exhibit a strong Raman response. A variety of candidate molecules may be used, such as para-mercaptoaniline, which can be bound to the surface of the nano particles and which yields three strong Stokes modes. Alternatively the nano particles can be embedded in a medium exhibiting a strong Raman response. The optical sampling geometry can be a layer deposited onto a reflective substrate exposed to incident light. Alternatively, the optical sampling geometry can be as a layer in a waveguide structure, where the Raman excitation is a result of the evanescent wave of the guided optical mode propagating in that structure.

According to some embodiments, the resonant nano particles are solid metal nano particles. The shape of the metal nano particles may be selected so as to adjust the wavelength of the resonance. Thus, contemplated shapes include spheroids, ellipsoids, needles, and the like. Further the metal nano particles may be aggregated into multiparticle aggregates so as to adjust the wavelength of the resonance. Still further, the metal nano particles may be embedded in a matrix material that is capable of adjusting the wavelength of the resonance. For example, the matrix may be any dielectric material suitable to form the core of a metal nano shell. More details on the nano shell sensor is described in Application Serial No. 20030174384, the content of which is incorporated by reference.

In one embodiment, the sensors are incorporated in an interferometer, and phase-modulated or interferometric optical sensors offer the highest sensitivity. Interferometric sensor systems typically employ the MachZehnder interferometer configuratio. Other configurations such as those of Michelson and Fabry-Perot can also be used. The interaction with the chemical substance takes place through the evanescent waves. The physical shape of the waveguide may change. The waveguide parameter changes due to a change in the physical dimension as well as to a change in the refractive index of the waveguide as a function of temperature. The intensity of the optical field decreases exponentially as it travels in the waveguide. The Kramers-Kronig relationship relates the imaginary part of the refractive index to its real part. Therefore, in attenuation mode chemical sensors, the phase of the guided mode also changes. The phase of the guided light may change. The TM and TE mode experience different phase shifts or attenuation.

One embodiment uses polarization of the light in sensing applications. The nano-sensor consists of an integrated difference (or polarimetric) interferometer that uses only one waveguide. The waveguide is designed to have only two modes of propagation: the fundamental TE and TM modes. A small portion of the waveguide's core where it contacts the measurand (a gas or a liquid) is exposed. The propagation constant of the TE and TM modes is sensitive to the refractive index of the sample. The dependence of each propagation constant on the refractive index of the sample is different and is dictated according to the equations for a three layer waveguide. At the output of the interferometer the light exiting the waveguide is passed through a polarizer at 45° and into a photodetector. After the polarizer, the waves arising from the original TE and TM are polarized in the same direction and may interfere.

In one embodiment, shape changes in a single DNA molecule bound to each sensor are detected and the result is compared against a database of substances (for example pathogens). If a match is found, the result is displayed.

In another embodiment, immobilized "probe" molecules of biological interest can be used. When exposed to an assay sample of interest, "target" molecules in the sample bind to the probe molecules to an extent determined by the concentration of the target molecule and its affinity for a particular probe molecule. If the target concentrations are known, the affinity of the target for the different probes can be estimated simultaneously. Conversely, given the known affinities of the different molecules in the target, the amounts of observed binding may be used to estimate simultaneously the concentrations of multiple analytes in the sample. United States Patent Application 20040002064 entitled "Toxin detection and compound screening using biological membrane microarrays" shows examples of the probe molecules of biological interest, the content of which is incorporated by reference.

In another embodiment, when a target molecule binds to the probe in the sensor, the probe molecule changes shape, and in its new conformation, pulls on the sensor. The motion of the sensor is detected using evanescent wave scattering, which analyzes light that leaks out behind a reflecting mirror. This evanescent wave is used to sense the position of an object "beyond" the mirror. Thus, conformational changes in a single DNA molecule at the nano meter scale are detected and the result is compared against a database of substances (for example pathogens). If a match is found, the result is displayed.

In another embodiment, the matrix can include Polymer Waveguide Chemical Sensors where both intrinsic and extrinsic sensing mechanisms are present. In this case, the optical waveguide itself is made of a nano-polymer that interacts with the chemical substance. The matrix is made from material that are able to absorb a target chemical onto the polymer surface. By diffusing into the waveguide the chemical is separated from the mixture. Thus, in this case, the waveguide is involved in both the separation process and the quantitative sensing of the target chemical.

In another embodiment, to increase the probing efficiency, optical energy inside the matrix is increased by operating the waveguide near its cut-off, or, more conveniently, by exciting surface plasmons. Light propagating inside the waveguide interacts with the charge density waves of a thin layer such as a metal like silver layer. If the guided wave's wavenumber matches that of the surface plasmon, the optical energy is absorbed by the plasmons and is consequently dissipated. The plasmon wavenumber, in turn, depends on the conductivity and can the surface condition of the metallic layer. A thin sensitive polymer film is usually deposited over the metallic film which, upon absorption of chemicals and gases, changes the plasmon wavenumber of the metallic film.

FIG. 7 is an exemplary diagram of an array of nano-based sensors. As shown in FIG. 7, a sensor includes a nano-cell sensor array 300. In the sensor array 300, first signal electrodes (chemical structure lines) 312 for selecting rows and second signal electrodes (bit lines) 316 for selecting columns are arranged to intersect at right angles. The first signal electrodes may be the bit lines and the second signal electrodes may be the chemical structure lines, differing from this example. A nano-sensor layer 314 is disposed at least between the first signal electrodes 312 and the second signal electrodes 316. Therefore, sensor cells 320, each of which includes a nano-sensor, are formed at intersections between the first signal electrodes 312 and the second signal electrodes 316. A peripheral circuit section 360 including a peripheral driver circuit for selectively allowing information to be read from the sensor cells and an amplifier circuit which for reading the information is also formed. The peripheral circuit section 360 includes a first driver circuit 350 for selectively controlling the first signal electrodes 312, a second driver circuit 352 for selectively controlling the second signal electrodes 316, and a signal detecting circuit (not shown) such as a sense amplifier, for example. As specific examples of the peripheral circuit section 360, a Y gate, a sense amplifier, an input-output buffer, an X address decoder, a Y address decoder, and an address buffer can be given. The peripheral circuit section 360 may be formed by MOS transistors formed on a substrate (single crystal silicon substrate, for example). In the case where the substrate is formed of a single crystal silicon substrate, the peripheral circuit section 360 can be integrated on the same substrate as the nano-sensor array 300. The nano-sensors are formed last by spin-coating a solution containing self-assembled nano-sensors on a wafer after the wafer has been processed and devices are formed using conventional semiconductor fabrication techniques. Conventional semiconductor structures are formed as is conventional. During the next to the last conventional step, gold electrodes are formed. Then a resist layer is formed over the last layer, and selective etching is performed to expose the gold electrodes. A solution containing the nano-sensors are spin-coated on top, where the nano-sensors self-assemble. Finally, a permeable layer is formed above the nano-sensors to protect the nano-elements and the semiconductor elements while allowing the target chemicals to pass through to the nano-sensors.

In one embodiment, the layer is a gas sensitive film containing or covering nano-elements such as nano-pores. As the sensitive film is exposed to different gases or chemicals, its resistance changes. The resistance of the film is measured by passing a small amount of current and monitoring the voltage drop across the film. In one device for sensing air quality, the sensor's film is readily oxidized (by $NO_2$ or $O_2$) or reduced (by CO or $NH_3$). Upon oxidation or reduction, the electrical resistivity (or some other physical parameter) of the matrix film changes and it is detected to infer the gas concentration. A heater can be provided near the matrix to provide temperature adjustments to better detect gas.

In yet another embodiment, the matrix is ultrasonically activated to detect gases and chemicals. In these embodiments, a gas or chemical sensitive nano-layer is deposited over an ultrasonic vibrator. When gases or chemicals are absorbed by the sensitive layer, they change the layer's mechanical properties. These mechanical changes influence the vibration amplitude and phase and can be picked up by monitoring the vibrational characteristics of the oscillator. In a microbalance embodiment, bulk wave detection is used to detect very small mass loading that occurs when minute quantities of materials are deposited over the surface of the oscillator. This method is the basis of thickness-monitors used in evaporation systems and can detect nano gram of materials. The surface acoustic wave embodiment is even more sensitive than the microbalance embodiment since it directly detects the surface loading. It can be used to detect simple mass loading effects and any mechanical changes that may occur in its gas or chemical sensitive layer. This method can detect changes as small as one part in billion.

For example, if desired, the nano-elements can be coated with a specific coating of interest (e.g., a ligand such as a peptide or protein, e.g., an enzyme), chosen for its ability to bind a particular ligand binding partner (e.g., an antibody or receptor can bind a ligand, or can themselves be the ligand to which ligand binding partner binds). Common analytes of interest for which detection is sought include glucose, cholesterol, warfarin, anthrax, testosterone, erythromycin, metabolites, pesticides, toxic molecules (e.g., formaldehyde, benzene, toluene, plutonium, etc.), ethanol (or other alcohols), pyruvate, and/or drugs.

For example, biosensors can include nano structures which capture or comprise enzymes such as oxidases, reductases, aldehyde/ketone reductases, alcohol dehydrogenases, aldehyde oxidases, cytochrome p450s, flavin monooxygenases, monoamine oxidases, xanthine oxidases, ester/amide hydrolases, epoxide hydrolases or their substrates or which capture their reaction products. Signal transduction is optionally facilitated by use of conductive polymers, to bind compounds to the nano structure, which facilitates electron transport to the surface of the structure. Several such polymers are available, including, e.g., polyaniline. It will be recognized that many of the biomolecules or other analytes to be captured (proteins, nucleic acids, lipids, carbohydrates) in the setting of a biosensor are charged, which can be used to cause them to "switch" a nano scale transistor, providing for detection of binding of an analyte.

In other embodiments, biomolecules such as enzymes generate signals that are detected by an array. For example, the array can include a glucose oxidase and/or a cholesterol oxidase enzyme for the detection of glucose or cholesterol levels in blood or other biological fluids. For example, a number of existing glucose monitoring systems exist, including ferrocene, ferricyanide and Osmium polymer mediated systems. These systems generally use glucose oxidases in the process of glucose detection. These systems are adapted to the present invention by mounting or capturing one or more analyte detection molecule (e.g., glucose oxidase or the relevant mediator) on a nano structure of interest. Similarly, in a biohazard detector, a p450 or other suitable enzyme can be used to detect the presence of warfarin or another relevant molecule of interest.

The binding of receptors and carbon nano tubes or biomolecules can be detected by an electrical method or resonance method or by using an x-y fluorescent laser reader. When the method of detecting an electrical signal is applied, the binding of receptors is detected by reading a minor change in voltage level of the carbon nano tubes occurring when the receptors or biomolecules are bound to the carbon nano tubes, using an appropriate circuit. In one environment, the nano tubes or nanostructures can be any conducting or semiconducting nanostructures. In some embodiments, the nanostructures can also be nanowires, nanorods, or some other elongated nanostructures. In particular, the nanostructures can be carbon nanotubes and may be single-wall, semiconducting, carbon nanotubes. There can be any number of nanostructures, some of which may intersect one another as they traverse the device, and some of which may traverse the device without intersection. A power supply applies a first voltage across the nanostructure sensing array. A first current through the nanostructure sensing array is measured with a meter. The nanostructure sensing array is exposed to an environment of interest. The electrical supply applies the same first voltage across the nanostructure sensing array and the gate voltage source applies the same first gate voltage to the substrate. A second current through the nanostructure sensing array is measured with the meter. Differences between the first current and the second current can be attributed to electrical changes in the nanostructure sensing array caused by interaction with an analyte. Electrical changes can be correlated to identification of particular analytes by comparing the changes with predetermined electrical changes made in know environments.

When the resonance detection method is applied, a nano plate structure designed to have a resonance frequency of a range from megaHertzs to low gigaHertzs is irradiated with a laser diode, and the binding of receptors or biomolecules to the nano plate structure is optically measured by detecting a reflection signal using a position detection photodiode. When the x-y fluorescent laser reader is used, the target biomolecules bound to receptors are reacted with, for example, fluorescent molecules or fluorescence-labeled antibodies, and the entire chip after the reaction with the target biomolecules is placed on the x-y fluorescent laser reader to detect fluorescence. a detection system for detecting the binding of receptors and carbon nano tubes or the binding of receptors and biomolecules may be further included. These types of binding can be detected by an electrical method or resonance method or by using an x-y fluorescent laser reader. When the method of detecting an electrical signal is applied, the binding of receptors or biomolecules is detected by reading a minor change in voltage level of the carbon nano tubes occurring when the receptors or biomolecules are bound to the carbon nano tubes, using an appropriate circuit. When the resonance detection method is applied, a nano plate structure designed to have a resonance frequency of a range from megaHertzs to low gigaHertzs is irradiated with a laser diode, and the binding of receptors or biomolecules to the nano plate structure is optically measured by detecting a reflection signal using a position detection photodiode. When the x-y fluorescent laser reader is used, the target biomolecules bound to receptors are reacted with, for example, fluorescent molecules or fluorescence-labeled antibodies, and the entire chip after the reaction with the target biomolecules is placed on the x-y fluorescent laser reader to detect fluorescence. In particular, the entire chip is scanned with a laser beam capable of exciting the fluorescence-labeled target proteins and imaged by using a charge-coupled device (CCD) capable of scanning the entire chip array. Alternatively, a confocal microscope, which increases automation and detects data rapidly at a high resolution, can be applied to collect data from the chip array.

Once digitized using the nano-sensors, various algorithms can be applied to detect a pattern associated with a substance. The chemical signal is parameterized into chemical features by a feature extractor. The output of the feature extractor is delivered to a sub-chemical structure recognizer. A structure preselector receives the prospective sub-structures from the recognizer and consults a dictionary to generate structure candidates. A syntax checker receives the structure candidates and selects the best candidate as being representative of the detected chemical. In case the chemical is a pathogen, suitable alarms can be sent.

With respect to the feature extractor, a wide range of techniques can be used, including the short time energy, the zero crossing rates, the level crossing rates, the filter-bank spectrum, the linear predictive coding (LPC), and the fractal method of analysis. In addition, vector quantization may be utilized in combination with any representation techniques. Further, one skilled in the art may use an auditory signal-processing model in place of the spectral models to enhance the system's robustness to noise and reverberation.

Nano Image Sensors

In another embodiment, the various nano devices can be integrated into image sensors for capture image information. Common image sensors include Charge Coupled Devices (CCD) and CMOS sensors. nano devices as described above can be used to act as photo collection components, charge transfer devices (such as CCD registers), and signal amplification devices in the image sensors.

Figure 8:
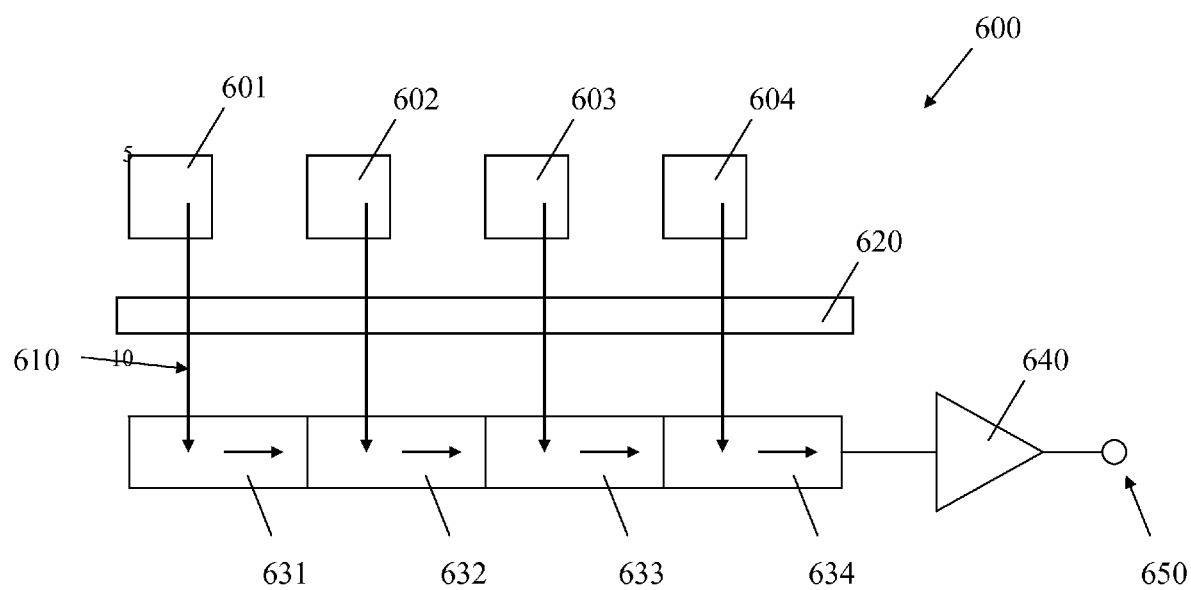
FIG. 8 is an exemplary diagram of an array of nano-based image sensors in accordance with the present invention.

Taking CCD sensors as an example, CCD image sensors can exist in different architectures such as Linear CCD array, Bi-Linear CCD array, Area CCD Sensor Array, and frame Transfer CCD, etc. The simplest architecture is a linear sensor. As shown in FIG. 8, the linear CCD array 600 consists of a line of photodiodes 601-604, each of which is respectively adjacent to a single CCD readout register 631-634. The charges collected by the photo diodes 601-604 are transferred (610) to CCD registers 631-634 under the control of the transfer gate 620. The charges collected are read out one pixel at a time at output signal 650 after the charge signals are converted to voltage signal by readout amplifier 640.

Although CCD architectures may be different, the basic operations of a CCD sensor all begin with the conversion of photons into electrons. When light is incident on the active area of the image sensor it interacts with the atoms that make up the silicon crystal. The energy transmitted by the light (photons) is used to enable an electron to excite to the conduction band and leaving a hole in the valence band. The more photons incident on the sensor, the more electron-hole pairs that are generated. High energy photons (short wavelengths) on the other hand are absorbed more closely to the surface of the sensor and may not reach the active part of the detector. Hence, there will be a spectrum over which the sensor will operate, falling off at short and long wavelengths.

The number of electrons generated per photon is known as the "quantum efficiency", or QE. The electrons can be separated from the holes in the photo collection areas. The amount of charge collected will depend on the light intensity, its spectrum and the integration time. By setting out a line or a 2D array of photo collection areas, it is possible to build up a representation of the image incident on the sensor.

In accordance with the present invention, a 1D or 2D array of image collection areas are patterned by the nano-elements made up of single-walled nano tubes aggregating (e.g., by van der Waals forces) in substantially parallel orientation to form a monolayer extending in directions substantially perpendicular to the orientation of the individual nano tubes. Such monolayer arrays can be formed by conventional techniques employing "self-assembled monolayers" (SAM) or Langmiur-Blodgett films. nano tubes 1 are bound to a substrate 2 having a reactive coating 3 (e.g., gold). Typically, SAMs are created on a substrate which can be a metal (such as gold, mercury or ITO (indium-tin-oxide)). The molecules of interest, here the SWNT molecules, are linked (usually covalently) to the substrate through a linker moiety. The linker moiety may be bound first to the substrate layer or first to single-wall nano tubes ("SWNT") molecule (at an open or closed end) to provide for reactive self-assembly. Langmiur-Blodgett films are formed at the interface between two phases, e.g., a hydrocarbon (e.g., benzene or toluene) and water. Orientation in the film is achieved by employing molecules or linkers that have hydrophilic and lipophilic moieties at opposite ends.

The 1D or 2D array of image collection areas can include photo diodes formed by PN-type junctions discussed in US Application Serial No. 20030200521, the content of which is incorporated herein by reference. The 1D or 2D nano sensor array can include arrays of crossed nanoscale wires having selectively programmable crosspoints. Nanoscale wires of one array are shared by other arrays, providing signal propagation between the arrays.

The nano elements can be patterned to form a 2D array for capturing an image-wise energy pattern from photons or energy particles. Each pattern nano element forms a photo diode with band gap sensitive to the photon energies the image sensor is designed to capture. At regular intervals photo induced charges at each pixel must be emptied and the amount of charge measured to determine the local light intensity. This is accomplished using a CCD register. A measuring device sits at the end of the row, known as the output node.

In another embodiment, the 1D or 2D array of image collection areas can include nano wires which are capable of capture photons and convert them into photoelectrons. The orientation of the nano wires can be controlled to maximize the photon detection efficiency. Methods of aligning nanowires are discussed in US Patent Publication 20030186522, the disclosure of which is incorporated hereof by reference.

In accordance with the present invention, the CCD registers and charge readout circuit, the readout amplifiers (for example, 620, 631-634, 640, 650) are fabricated in one or more layers made of semiconductor materials such as silicon and silicon oxide using conventional semiconductor microfabrication technologies. The image sensitive image layer (comprising photo diodes 601-604) patterned with nano materials is formed over the layers of the semiconductor materials.

The charges in an image collection area, or a pixel, is transferred into a measuring device in the semiconductor layer to produce a signal that depends on the amount of stored charge. The charge transfer is controlled by the transfer gate 620 at a predetermined clock rate. The empty image collection area in the nano layer is ready for capturing the next image. The downward charge transfer from the nano photo sensitive layer to the semiconductor charge measuring layer is similar to the frame transfer CCD architecture. Detailed operations of photo induced charge transfers and readout are discussed in U.S. Pat. Nos. 5,946,034 and 6,576,938, the disclosures of which are incorporated hereof by reference.

The nano-semiconductor CCD device as described above has the following advantages. Since the photon sensing pixels occupy the nano photo sensitive layer on top, no photon receiving area needs to be wasted for building CCD registers and voltage conversion devices. The effective spatial fraction of image sensing can be maximized to 80-95% range. Another advantage of the nano-semiconductor CCD device in the present invention is the frame fresh rate is significantly increased because photo induced charges are transfer directly to the CCD registers, rather than cascade transferred between photo charge collection areas. These advantages are critical for fabricating miniature and high speed imaging devices such as digital cameras, digital video cameras, night vision devices, telescope cameras, and microscopic cameras for scientific observations.

In accordance to another embodiment of the present invention, the nano-semiconductor imaging device can be sensitive to different photo spectrum such red, green, blue, infrared, UV etc. by using color filter arrays (CFA) disposed over the nano photo sensitive layer. Different CFA patterns include Bayer pattern, interlaced liner pattern etc. The semiconductor layer can further include electronic circuit for constructing color planes from the photo-induced charges filtered by CFA. The electronic circuit can also perform various image processing operations well known in the art. Detailed operations of CFA patterns and improvement are discussed in U.S. Pat. No. 6,366,318, the disclosures of which are incorporated hereof by reference.

In another embodiment, nano-elements are fabricated above a CMOS image sensor where each pixel contains three transistors: a select transistor, a source follower transistor and a reset transistor. The source follower transistor is connected to a photodiode with a nano-element formed above the photodiode. Light is collected by the photodiode/nano-element causes a change in the potential on the photodiode which is read out through the action of the select and source follower transistors. The reset transistor is used to establish a constant potential on the photodiodes prior to the start of exposure to light. In one embodiment, the nano-element is an FSA assembled geometric structure with a specific optical absorption spectrum, a specific optical transmission spectrum, a specific optical reflection characteristic, or a capability for modifying the polarization of light. In another embodiment, fullerene nano tubes such as an (n,n) tube can be used in conjunction with other materials can be used to form a Schottky barrier which would act as a light harvesting sensor or antenna. In one embodiment, a (10, 10) tube can be connected via sulfur linkages to gold at one end of the tube and lithium at the other end of the tube forming a natural Schottky barrier. Current is generated through photo conductivity. As the (10, 10) tube acts like an antenna, it pumps electrons into one electrode, but back flow of electrons is prevented by the intrinsic rectifying diode nature of the nano tube/metal contact. In forming an antenna, the length of the nano tube can be varied to achieve any desired resultant electrical length. The length of the molecule is chosen so that the current flowing within the molecule interacts with an electromagnetic field within the vicinity of the molecule, transferring energy from that electromagnetic field to electrical current in the molecule to energy in the electromagnetic field. This electrical length can be chosen to maximize the current induced in the antenna circuit for any desired frequency range. Or, the electrical length of antenna element can be chosen to maximize the voltage in the antenna circuit for a desired frequency range. Additionally, a compromise between maximum current and maximum voltage can be designed. More on the fullerene light sensor is disclosed in Application Serial No. 20020150524, the content of which is incorporated by reference.

The nano image sensor is eventually connected to various other imaging devices such as a stand-alone digital camera (both still and video cameras), and embedded digital cameras (that may be used in cellular phones, personal digital assistants (PDA) and the like). In another example implementation, various imaging devices may be coupled to image sensor package, including digital still cameras, tethered PC cameras, imaging enabled mobile devices (e.g. cell phones, pagers, PDA's and laptop computers), surveillance cameras, toys, machine vision systems, medical devices and image sensors for automotive applications.

In yet another embodiment, an array of electrically conductive carbon nano tube (CNT) towers are grown directly on the surface of a silicon chip. The CNT towers allow signals captured from a charge-coupled device (CCD) to be transmitted directly to the neural elements of the retina to restore vision. A retinal electrode array with a remote return electrode is provided outside of the eye. An array of stimulating nano-electrodes is placed on the retinal surface (epiretinally) or under the retina (subretinally) and a relatively large return electrode is placed outside of the sclera and distant from the array of stimulating electrodes. The remote return electrode promotes deeper stimulation of retinal tissue to support vision.

The structures discussed above to recognize chemical substances can be applied to recognize images as well. Such structures include HMMs, neural networks, fuzzy logic, and statistical recognizers, among others.

Nano Displays

Turning now to a different embodiment to display images, the nano-elements can be light-emitting nano particles. The production of a robust, chemically stable, crystalline, passivated nano particle and composition containing the same, that emit light with high efficiencies and size-tunable and excitation energy tunable color is discussed in Application Serial No. 20030003300, the content of which is hereby incorporated b reference. The methods include the thermal degradation of a precursor molecule in the presence of a capping agent at high temperature and elevated pressure. A particular composition prepared by the methods is a passivated silicon nano particle composition displaying discrete optical transitions. Group IV metals form nano crystalline or amorphous particles by the thermal degradation of a precursor molecule in the presence of molecules that bind to the particle surface, referred to as a capping agent at high temperature and elevated pressure. In certain embodiments, the reaction may run under an inert atmosphere. In certain embodiments the reaction may be run at ambient pressures. The particles may be robust, chemically stable, crystalline, or amorphous and organic-monolayer passivated, or chemically coated by a mixture of organic molecules. In one embodiment, the particles emit light in the ultraviolet wavelengths. In another embodiment, the particles emit light in the visible wavelengths. In other embodiments, the particles emit light in the near-infrared and the infrared wavelengths. The particles may emit light with high efficiencies. Color of the light emitted by the particles may be size-tunable and excitation energy tunable. The light emission may be tuned by particle size, with smaller particles emitting higher energy than larger particles. The surface chemistry may also be modified to tune the optical properties of the particles. In one embodiment, the surfaces may be well-passivated for light emission at higher energies than particles with surfaces that are not well-passivated. The average diameter of the particles may be between 1 and 10 nm. A particular composition prepared by the methods is a passivated silicon nano particle composition displaying discrete optical transitions and photoluminescence.

In another embodiment, a light may be formed having a broad size distribution of silicon nano particles. The broad size distribution may be advantageous in that the combination of wavelengths emitted by the different size particles may produce a white light. The silicon nano particles may be embedded in a polymer matrix. The polymer matrix is not, however, necessary for the silicon nano particles to function effectively as the emissive layer. The size distribution of silicon nano particles may allow the emission of white light. The nano particles themselves may emit with size-independent quantum yields and lifetimes. Clusters of nano particles may produce a broad emission band. If energy transfer occurs between neighboring nano particles, it does not result in the selective emission from only the largest particles with the lowest energy gap between the highest occupied and lowest unoccupied molecular orbits (HOMO and LUMO). This situation is qualitatively different than known technology using CdSe nano particles.

An embodiment of a basic design for light emitting device includes a first electrode, second electrode, and emissive layer. Emissive layer may include the nano particles exhibiting discrete optical properties as described herein. Emissive layer may include a polymer wherein the nano particles may be suspended. However, nano particle based light emitting devices may not require a polymer to emit, in contrast to many organic LEDs. Polymers may inflict losses through absorption, scattering, and poor electron-hole interfaces. Emissive layer may be positioned adjacent first electrode. First electrode may function as a cathode. Emissive layer may be positioned adjacent second electrode. Second electrode may function as an anode. Substrate may include a transparent conductive oxide layer. Non-limiting examples of the transparent conductive oxide layer may include indium tin oxide, tin oxide, or a translucent thin layer of Ni or Au or an alloy of Ni and Au. The basic design of light emitting devices is described in further detail in U.S. Pat. No. 5,977,565 which is incorporated herein by reference. The nano particles may emit light by optical stimulation. In this device, an optical excitation source is used in place of electrical stimulation. However, in another embodiment, a combination of optical excitation and electrical stimulation may be used to enhance device performance, such as overall energy efficiency or perhaps color tenability.

The nano display device in the present invention can include an array of light-emitting cells disposed in rows and columns and constructed over a substrate. Each light emitting cell comprises a first electrode, a second electrode, and a light-emitting nano material disposed in the intersecting region between the first electrode and the second electrode. The light-emitting nano material is capable of emitting light when a voltage is applied between the first electrode and the second electrode. The nano display device of claim 1, wherein the light-emitting nano material includes low molecular weight or polymeric organic molecules, and nano particles formed by semiconductor materials as described below. The light-emitting nano material can emit photons at one or more wavelengths for example in the Ultra Violet, visible, and infrared spectra. A light emitting diode is formed in each light-emitting cell by the light-emitting nano material, the first electrode, and the second electrode. A nano diode can be fabricated using techniques above. The light-emitting cells are insulated by insulation regions so that each light-emitting cell can be individually addressed for light emission.

In another embodiment, a molecule is used as light emitter with two electrodes at a tunneling distance from each other. Such a tunneling distance may as well lie in the subnanometer range as above that range and is the distance which allows a tunneling current to flow between the electrodes. As discussed in US Application Serial 20020096633, the content of which is incorporated by reference, the molecule can have a tertiary-butyl substituted tetracycline with the tetracycline as the central entity and the tertiary butyls as the peripheral entities which are movable with respect to the central entity. The molecule has several stable or metastable conformations depending on the states of its entities. These states are determined by the inner binding forces of the molecule, i.e. between the peripheral entities and the central entity, and the binding forces between the entities and the environment. The molecule is situated preferably on a crystalline substrate which serves as one of the electrodes. Hence, the inner forces of the molecule and the forces towards the substrate determine the conformations. In a first conformation the peripheral entities have a binding force towards tile substrate which dominates over the force between the central entity and the substrate. With other words, the central entity is so far away from the substrate that the force between it and the substrate is weaker than the force between the substrate and the peripheral entities. The binding force between the peripheral entities and the substrate are however sufficiently weak that the molecule is not fixed in its horizontal position. It therefore floats around on the substrate surface at room temperature. Another conformation is dominated by the force between the central entity and the substrate. The central entity is then near enough at the substrate that the binding force holds the central entity to the substrate. In this conformation, the molecule remains in its position, therefore it is also called the pinned conformation. The peripheral entities in this conformation are somehow distorted or bent or more generally moved from their equilibration position, i.e. the position which they had in the first conformation. The holding force between the central entity and the substrate is stronger than eventual restoring forces between the peripheral entities and the central entity which try to form the molecule back to the first conformation. The molecule is immobilized by the combined force between the substrate and the central entity and between the peripheral entities and the substrate. The molecule can be switched between the two stable conformations. The switching is induced by electrical voltage but can also occur through mechanical energy. The switching is reversible. However, also irreversible switching is possible for selected molecule types. When an electrical current is allowed to flow through the substrate, light emission occurs. The substrate may have a predetermined surface structure, namely for a crystalline substrate the crystalline plane in which it lies. Light emission occurs on various planes, such as the {111} and the {100} plane. Copper, gold or silver are exemplary substrate materials on which the effect can be seen. Other materials for the substrate, such as polycrystalline materials or amorphous materials work as well.

In another embodiment, the light emitter nano-elements can be inorganic nanocrystals. The crystal composition includes a solvent with semiconductor nanoparticles in the solvent, wherein the solvent and the semiconductor nanoparticles are in an effective amount in the liquid crystal composition to form a liquid crystalline phase. The semiconductor nanoparticles can be rod-shaped or disk-shaped, and has an aspect ratio greater than about 2:1 or less than about 1:2. As discussed in Application Serial No. 20030136943, the content of which is incorporated by reference, the nanocrystals are treated as a conventional polymer or biological macromolecule from the assembly point of view. This enables a wide range of chemical macromolecular assembly techniques to be extended to inorganic solids, which possess a diverse range of optical, electrical, and magnetic properties. The optical properties of the semiconductor nanoparticles can depend upon their diameters and lengths. The photoluminescence wavelengths produced by the semiconductor nanoparticles can be tuned over the visible range by variation of the particle size, and the degree of polarization can be controlled by variation of the aspect ratio. Accordingly, by tuning the size of the semiconductor nano particles, the liquid crystal compositions may emit different colors (i.e., different wavelengths of light). For instance, when the semiconductor nano particles in the liquid crystal composition are about 3 nanometers wide and are about 5 nanometers long, the liquid crystal composition can produce green light. When the semiconductor nano particles in the liquid crystal composition are about 3 nanometers wide and are about 60 nanometers long, the liquid crystal composition can produce orange light. When the semiconductor nano particles in the liquid crystal composition are about 4 nanometers wide and about 6 nanometers long, the liquid crystal composition can produce red light. Accordingly, in embodiments of the invention, the optical properties of the liquid crystal composition can be "tuned" by adjusting the size of the nano particles in the liquid crystal composition.

Also, because the semiconductor nano particles are aligned in embodiments of the invention, any light that is produced by the aligned semiconductor nano particles can be polarized. The semiconductor nano particles may comprise any suitable semiconductor material. For example, suitable semiconductors include compound semiconductors. Suitable compound semiconductors include Group II-VI semiconducting compounds such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe. Other suitable compound semiconductors include Group III-V semiconductors such as GaAs, GaP, GaAs—P, GaSb, InAs, InP, InSb, AlAs, AlP, and AlSb. The use of Group IV semiconductors such as germanium or silicon may also be feasible under certain conditions.

In another embodiment, a nano-light emitting faceplate patterned with colored-light-emitting nano pixels having a predetermined size, pattern and spacing, the nano-light color emitters eliminates the need for polarizers and color filters in the Liquid Crystal Displays, which increases the efficiency of light transmission, and increase brightness and contrast, and reduces power consumption. The pattern of nano pixels in patterns for emitting different color light can be achieved a sequence spin coating steps. For example, a layer of green-photon emitting nano materials is first spin coated over nano binding areas that is in a 2D pattern as described above. The excess green emitting nano material is removed. A second pattern of nano binding materials is formed on the substrate over the areas that is not covered by the green-photon emitting nano materials. The nano binding materials at this step may be specific to a blue-photon emitting material that is subsequently spin coated. The excess blue-photon emitting material is removed. A red-photon emitting material is coated finally in similar steps to complete the color emitting pattern for a full color display.

In another embodiment, electronic display can be achieved by modulating reflective index or the orientations of the reflective axes of the nano-elements on light reflective or refractive surfaces. The modulation of the reflective index of the nano materials can be driven by a two dimensional array of electrode pairs and driver circuits as in the conventional electronic display system. Each pair of electrodes and the associated nano material define an image pixel. The reflective index of the nano materials can be spatially modulated by selectively switching on and off of the electrode pairs at different pixel locations, therefore defining an image-wise pattern. An projective electronic nano display is obtained by illuminating an uniform light beam across the nano reflective (or refractive) surfaces. In summary, the nano display device includes an array of light-emitting cells disposed in rows and columns and constructed over a substrate. Each light emitting cell comprises a first electrode, a second electrode, and a light-reflective or light-refractive nano material disposed in the intersecting region between the first electrode and the second electrode. The light-reflective or light-refractive nano material is capable of deflecting light when a voltage is applied between the first electrode and the second electrode.

The nano display devices can include driver circuits for driving rows and columns electrodes, digital signal processing units, memory, display mode control, power drivers which are typically found in conventional electronic displays. The nano display devices can include driver circuits for driving rows and columns electrodes, digital signal processing units, memory, display mode control, power drivers which are typically found in conventional electronic displays. The display component is mounted on an interconnect substrate, usually flex, and electrical connections are made from the edge of the CMOS back plane to the substrate. Finally, the display component is suitably encapsulated, thus providing environmental protection. Plastic encapsulation is typically used in consumer products. The resulting display modules produced in this manner are compact, lightweight, and relatively inexpensive.

The magnification of the image can be accomplished using refractive or reflective lens assemblies that are well known and widely utilized in standard optical projection systems.

Nano Solar Cells

Figure 9:
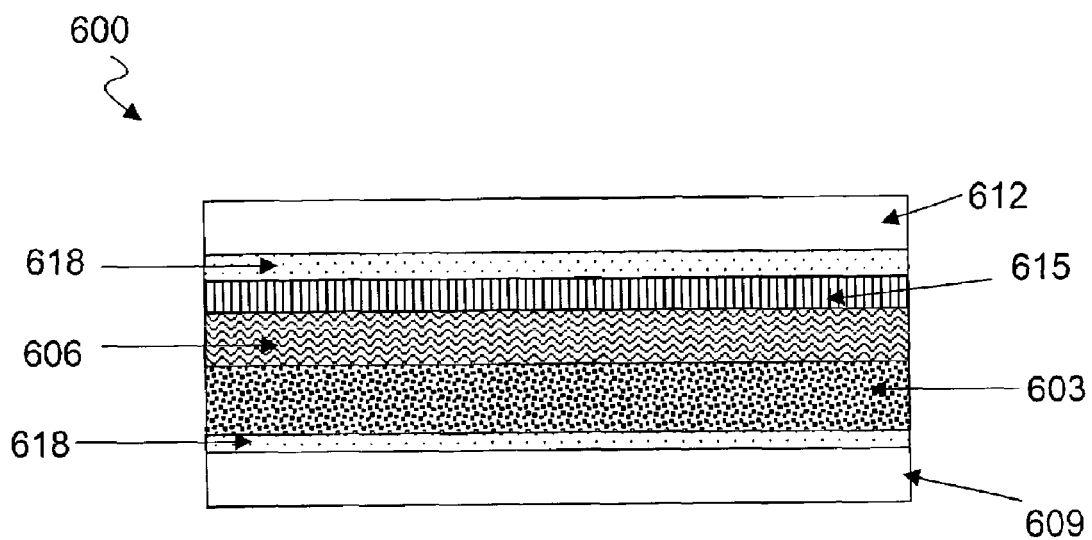
FIG. 9 depicts a cross-sectional view of a flexible photovoltaic cell.

The nano-elements can be used as a solar cell as well. FIG. 9 depicts a flexible photovoltaic cell 600, in accordance with the invention, that includes a photosensitized interconnected nanoparticle material 603 and a charge carrier material 606 disposed between a first flexible, significantly light transmitting substrate 609 and a second flexible, significantly light transmitting substrate 612. In one embodiment, the flexible photovoltaic cell further includes a catalytic media layer 615 disposed between the first substrate 609 and second substrate 612. Preferably, the photovoltaic cell 600 also includes an electrical conductor 618 deposited on one or both of the substrates 609 and 612. The methods of nano particle interconnection provided herein enable construction of the flexible photovoltaic cell 600 at temperatures and heating times compatible with such substrates 609 and 612. The flexible, significantly light transmitting substrates 609 and 612 of the photovoltaic cell 600 preferably include polymeric materials.

Suitable substrate materials include, but are not limited to, PET, polyimide, PEN, polymeric hydrocarbons, cellulosics, or combinations thereof. Further, the substrates 609 and 612 may include materials that facilitate the fabrication of photovoltaic cells by a continuous manufacturing process such as, for example, a roll-to-roll or web process as discussed in US Application Serial No. 20030189402, the content of which is incorporated by reference. The substrate 609 and 612 may be colored or colorless. Preferably, the substrates 609 and 612 are clear and transparent. The substrates 609 and 612 may have one or more substantially planar surfaces or may be substantially non-planar. For example, a non-planar substrate may have a curved or stepped surface (e.g., to form a Fresnel lens) or be otherwise patterned.

An electrical conductor 618 is deposited on one or both of the substrates 609 and 612. Preferably, the electrical conductor 618 is a significantly light transmitting material such as, for example, ITO, a fluorine-doped tin oxide, tin oxide, zinc oxide, or the like. In one illustrative embodiment, the electrical conductor 618 is deposited as a layer between about 100 nm and about 500 nm thick. In another illustrative embodiment, the electrical conductor 618 is between about 150 nm and about 300 nm thick. According to a further feature of the illustrative embodiment, a wire or lead line may be connected to the electrical conductor 618 to electrically connect the photovoltaic cell 600 to an external load.

As noted in Application Serial No. 20030189402, metal oxide nanoparticles are interconnected by contacting the nanoparticles with a suitable polylinker dispersed in a suitable solvent at or below room temperature or at elevated temperatures below about 300° C. The nanoparticles may be contacted with a polylinker solution in many ways. For example, a nanoparticle film may be formed on a substrate and then dipped into a polylinker solution. A nanoparticle film may be formed on a substrate and the polylinker solution sprayed on the film. The polylinker and nanoparticles may be dispersed together in a solution and the solution deposited on a substrate. To prepare nanoparticle dispersions, techniques such as, for example, microfluidizing, attritting, and ball milling may be used. Further, a polylinker solution may be deposited on a substrate and a nanoparticle film deposited on the polylinker. The photosensitized interconnected nanoparticle material 603 may include one or more types of metal oxide nanotubes, as described in detail above. Preferably, the nanotubes contain titanium dioxide particles having an average particle size of about 20 nm. A wide variety of photosensitizing agents may be applied to and/or associated with the nanotubes to produce the photosensitized interconnected nanotube material 603. The photosensitizing agent facilitates conversion of incident visible light into electricity to produce the desired photovoltaic effect. It is believed that the photosensitizing agent absorbs incident light resulting in the excitation of electrons in the photosensitizing agent. The energy of the excited electrons is then transferred from the excitation levels of the photosensitizing agent into a conduction band of the interconnected nanotubes 603. This electron transfer results in an effective separation of charge and the desired photovoltaic effect. Accordingly, the electrons in the conduction band of the interconnected nanotubes are made available to drive an external load electrically connected to the photovoltaic cell. In one illustrative embodiment, the photosensitizing agent is sorbed (e.g., chemisorbed and/or physisorbed) on the interconnected nanotubes 603. The photosensitizing agent may be sorbed on the surfaces of the interconnected nanotubes 603, throughout the interconnected nanotubes 603, or both. The photosensitizing agent is selected, for example, based on its ability to absorb photons in a wavelength range of operation, its ability to produce free electrons (or electron holes) in a conduction band of the interconnected nanotubes 603, and its effectiveness in complexing with or sorbing to the interconnected nanotubes 603. The charge carrier material 606 portion of the photovoltaic cells may form a layer in the photovoltaic cell, be interspersed with the material that forms the photosensitized interconnected nanotube material 603, or be a combination of both. The charge carrier material 606 may be any material that facilitates the transfer of electrical charge from a ground potential or a current source to the interconnected nanotubes 603 (and/or a photosensitizing agent associated therewith). A general class of suitable charge carrier materials can include, but are not limited to solvent based liquid electrolytes, polyelectrolytes, polymeric electrolytes, solid electrolytes, n-type and p-type transporting materials (e.g., conducting polymers), and gel electrolytes.

In another embodiment, nanocrystalline $TiO_2$ is replaced by a monolayer molecular array of short carbon nanotube molecules. The photoactive dye need not be employed since the light energy striking the tubes will be converted into an oscillating electronic current which travels along the tube length. The ability to provide a large charge separation (the length of the tubes in the array) creates a highly efficient cell. A photoactive dye (such as cis-[bisthiacyanato bis(4,4'-dicarboxy-2,2'-bipyridine Ru (II))] can be attached to the end of each nanotube in the array to further enhance the efficiency of the cell. In another embodiment of the present invention, the $TiO_2$ nanostructure described by Grtzel in U.S. Pat. No. 5,084,365 (incorporated herein by reference in its entirety) can serve as an underlying support for assembling an array of SWNT molecules. In this embodiment, SWNTs are attached directly to the $TiO_2$ (by absorptive forces) or first derivatized to provide a linking moiety and then bound to the TiO.sub.2 surface. This structure can be used with or without a photoactive dye as described above.

In yet another embodiment, instead of nanotubes, shape-controlled inorganic nanocrystals can be used. Shape-controlled inorganic nanocrystals offer controlled synthesis that allows not only the prediction of a structure based on computer models, but also the prediction of a precise synthetic recipe that produces that exact structure in high-purity and high-yield, with every particle identical to every other particle. Inorganic semiconductor nanocrystals can control variables such as length, diameter, crystallinity, doping density, heterojunction formation and most importantly composition. Inorganic semiconductor nanocrystals can be fabricated from all of the industrially important semiconductor materials, including all of the Group III-V, Group II-VI and Group IV materials and their alloys, as well as the transition metal oxides. Furthermore, the inorganic semiconductor nanostructures can be fabricated such that material characteristics change controllably throughout the nanostructure to engineer additional functionality (i.e. heterostructures) and complexity into the nanostructure. As discussed in US Application Serial No. 20030145779, three dimensional tetrapods may be important alternatives to nanocrystal fibers and rods as additives for mechanical reinforcement of polymers (e.g., polymeric binders including polyethylene, polypropylene, epoxy functional resins, etc.). Tetrapod shaped nanocrystal particles, for example, can interlock with each other and can serve as a better reinforcing filler in a composite material (e.g., with a binder), than for example, nanospheres. The nanocrystal particles can be mixed with the binder using any suitable mixing apparatus. After the composite material is formed, the composite material can be coated on a substrate, shaped, or further processed in any suitable manner.

An exemplary photovoltaic device may have nanocrystal particles in a binder. This combination can then be sandwiched between two electrodes (e.g., an aluminum electrode and an indium tin oxide electrode) on a substrate to form a photovoltaic device. Two separate mixtures can be used: one containing inorganic semiconductors made of cadmium selenide (CdSe) nanorod molecules and one containing the organic polymer to be blended with the nanorods. The mixtures are then combined and spin-cast at room temperature to produce an even film of nanorods that's approximately 200 nanometers thick—about a thousandth the thickness of a human hair. Tetrapods also have independent tunability of the arm length and the band gap, which is attractive for nanocrystal based solar cells or other types of photovoltaic devices. In comparison to nanocrystal particles that are randomly oriented, the tetrapods are aligned and can provide for a more unidirectional current path than randomly oriented nanocrystal particles.

In one embodiment, each flexible photovoltaic cell further includes one or more flexible light-transmitting substrates, a photosensitized interconnected nanoparticle material, and an electrolyte redox system. In general, the nanotube material and the electrolyte redox system are both disposed between the first and second substrates. The flexible base may be the first significantly light-transmitting substrate of the flexible photovoltaic cell. In one embodiment, the flexible photovoltaic cell further includes a photosensitized nanomatrix layer and a charge carrier medium. The photovoltaic cell may energize the display element directly, or may instead charge a power source in electrical communication with the display element. The display apparatus may further include an addressable processor and/or computer interface, operably connected to the at least one photovoltaic cell, for controlling (or facilitating control of) the display element.

"Semiconductor-nanocrystal" includes semiconducting crystalline particles of all shapes and sizes. They can have at least one dimension less than about 100 nanometers, but they are not so limited. Rods may be of any length. "Nanocrystal", "nanorod" and "nanoparticle" can be used interchangeably herein. In some embodiments of the invention, the nanocrystal particles may have two or more dimensions that are less than about 100 nanometers. The nanocrystals may be core/shell type or core type. For example, some branched nanocrystal particles according to some embodiments of the invention can have arms that have aspect ratios greater than about 1. In other embodiments, the arms can have aspect ratios greater than about 5, and in some cases, greater than about 10, etc. The widths of the arms may be less than about 200, 100, and even 50 nanometers in some embodiments. For instance, in an exemplary tetrapod with a core and four arms, the core can have a diameter from about 3 to about 4 nanometers, and each arm can have a length of from about 4 to about 50, 100, 200, 500, and even greater than about 1000 nanometers. Of course, the tetrapods and other nanocrystal particles described herein can have other suitable dimensions. In embodiments of the invention, the nanocrystal particles may be single crystalline or polycrystalline in nature.

IC Packaging

The foregoing electronic devices are generally housed in a package including a chip with a plurality of chip pads formed on the chip as input/output ports for a variety of signals. A lead frame includes a plurality of contact points which are electrically connected to the chip pads to receive the variety of signals from or to output the same to an external circuit. Further, bonding wires electrically connect each chip pad to its respective contact points on the lead frame. The bonding wires comprise one or more of nano material such as Fullerene molecules, nanotubes, nanowires, nanocomposite material, nanostructured carbon material as described below.

The structure of the package is protected by, for example, a nano-ceramic power compound or resin as described below to remove heat.

Fullerene molecular wires are used to replace conventional bonding wires. In one embodiment, the bonding wires can be FSAs or selfassembly assisted by binding to FSA or fullerene nano-wires. Choice of FSAs can also enable self-assembly of compositions whose geometry imparts useful chemical or electrochemical properties including operation as a catalyst for chemical or electrochemical reactions, sorption of specific chemicals, or resistance to attack by specific chemicals, energy storage or resistance to corrosion. Examples of biological properties of FSA self-assembled geometric compositions include operation as a catalyst for biochemical reactions; sorption or reaction site specific biological chemicals, agents or structures; service as a pharmaceutical or therapeutic substance; interaction with living tissue or lack of interaction with living tissue; or as an agent for enabling any form of growth of biological systems as an agent for interaction with electrical, chemical, physical or optical functions of any known biological systems.

FSA assembled geometric structures can also have useful mechanical properties which include but are not limited to a high elastic to modulus weight ratio or a specific elastic stress tensor. Self-assembled structures, or fullerene molecules, alone or in cooperation with one another (the collective set of alternatives will be referred to as "molecule/structure") can be used to create devices with useful properties. For example, the molecule/structure can be attached by physical, chemical, electrostatic, or magnetic means to another structure causing a communication of information by physical, chemical, electrical, optical or biological means between the molecule/structure and other structure to which the molecule/structure is attached or between entities in the vicinity of the molecule/structure. Examples include, but are not limited to, physical communication via magnetic interaction, chemical communication via action of electrolytes or transmission of chemical agents through a solution, electrical communication via transfer of electronic charge, optical communication via interaction with and passage of any form with biological agents between the molecule/structure and another entity with which those agents interact.

The bonding wires can also act as antennas. For example, the lengths, location, and orientation of the molecules can be determined by FSAs so that an electromagnetic field in the vicinity of the molecules induces electrical currents with some known phase relationship within two or more molecules. The spatial, angular and frequency distribution of the electromagnetic field determines the response of the currents within the molecules. The currents induced within the molecules bear a phase relationship determined by the geometry of the array. In addition, application of the FSAs could be used to facilitate interaction between individual tubes or groups of tubes and other entities, which interaction provides any form of communication of stress, strain, electrical signals, electrical currents, or electromagnetic interaction. This interaction provides an "interface" between the self-assembled nano structure and other known useful devices. In forming an antenna, the length of the nano tube can be varied to achieve any desired resultant electrical length. The length of the molecule is chosen so that the current flowing within the molecule interacts with an electromagnetic field within the vicinity of the molecule, transferring energy from that electromagnetic field to electrical current in the molecule to energy in the electromagnetic field. This electrical length can be chosen to maximize the current induced in the antenna circuit for any desired frequency range. Or, the electrical length of an antenna element can be chosen to maximize the voltage in the antenna circuit for a desired frequency range. Additionally, a compromise between maximum current and maximum voltage can be designed. A Fullerene nano tube antenna can also serve as the load for a circuit. The current to the antenna can be varied to produce desired electric and magnetic fields. The length of the nano tube can be varied to provide desired propagation characteristics. Also, the diameter of the antenna elements can be varied by combining an optimum number of strands of nano tubes. Further, these individual nano tube antenna elements can be combined to form an antenna array. The lengths, location, and orientation of the molecules are chosen so that electrical currents within two or more of the molecules act coherently with some known phase relationship, producing or altering an electromagnetic field in the vicinity of the molecules. This coherent interaction of the currents within the molecules acts to define, alter, control, or select the spatial, angular and frequency distributions of the electromagnetic field intensity produced by the action of these currents flowing in the molecules. In another embodiment, the currents induced within the molecules bear a phase relationship determined by the geometry of the array, and these currents themselves produce a secondary electromagnetic field, which is radiated from the array, having a spatial, angular and frequency distribution that is determined by the geometry of the array and its elements. One method of forming antenna arrays is the self-assembly monolayer techniques discussed above.

Various molecules or nano-elements can be coupled to one or more electrodes in a layer of an IC substrate using standard methods well known to those of skill in the art. The coupling can be a direct attachment of the molecule to the electrode, or an indirect attachment (e.g. via a linker). The attachment can be a covalent linkage, an ionic linkage, a linkage driven by hydrogen bonding or can involve no actual chemical attachment, but simply a juxtaposition of the electrode to the molecule. In some preferred embodiments, a "linker" is used to attach the molecule(s) to the electrode. The linker can be electrically conductive or it can be short enough that electrons can pass directly or indirectly between the electrode and a molecule of the storage medium. The manner of linking a wide variety of compounds to various surfaces is well known and is amply illustrated in the literature. Means of coupling the molecules will be recognized by those of skill in the art. The linkage of the storage medium to a surface can be covalent, or by ionic or other non-covalent interactions. The surface and/or the molecule(s) may be specifically derivatized to provide convenient linking groups (e.g. sulfur, hydroxyl, amino, etc.). In one embodiment, the molecules or nano-elements self-assemble on the desired electrode. Thus, for example, where the working electrode is gold, molecules bearing thiol groups or bearing linkers having thiol groups will self-assemble on the gold surface. Where there is more than one gold electrode, the molecules can be drawn to the desired surface by placing an appropriate (e.g. attractive) charge on the electrode to which they are to be attached and/or placing a "repellant" charge on the electrode that is not to be so coupled.

The FSA bonding wires can be used alone or in conjunction with other elements. A first group of elements includes palladium (Pd), rhodium (Rh), platinum (Pt), and iridium (Ir). As noted in US Patent Application Serial No. 20030209810, in certain situations, the chip pad is formed of aluminum (Al). Accordingly, when a gold-silver (Au—Ag) alloy bonding wire is attached to the chip pad, the Au of the bonding wire diffuses into the chip pad, thereby resulting in a void near the neck. The nano-bonding wire, singly or in combination with the elements of the first group form a barrier layer in the interface between a Au-rich region (bonding wire region) and an Al-rich region (chip pad region) after wire bonding, to prevent diffusion of Au and Ag atoms, thereby suppressing intermetallic compound and Kirkendall void formation. As a result, a reduction in thermal reliability is prevented.

Nano-bonding wires can also be used singly or in combination with a second group of elements that includes boron (B), beryllium (Be), and calcium (Ca). The elements of the second group enhances tensile strength at room temperature and high temperature and suppresses bending or deformation of loops, such as sagging or sweeping, after loop formation. When an ultra low loop is formed, the elements of the second group increase yield strength near the ball neck, and thus reduce or prevent a rupture of the ball neck. Especially, when the bonding wire has a small diameter, a brittle failure near the ball neck can be suppressed.

Nano-bonding wires can also be used singly or in combination with a third group of elements that includes phosphorous (P), antimony (Sb), and bismuth (Bi). The elements of the third group are uniformly dispersed in a Au solid solution to generate a stress field in the gold lattice and thus to enhance the strength of the gold at room temperature. The elements of the third group enhance the tensile strength of the bonding wire and effectively stabilize loop shape and reduce a loop height deviation.

Nano-bonding wires can also be used singly or in combination with a fourth group of elements that includes magnesium (Mg), thallium (Tl), zinc (Zn), and tin (Sn). The elements of the fourth group suppress the grain refinement in a free air ball and soften the ball, thereby preventing chip cracking, which is a problem of Au—Ag alloys, and improving thermal reliability.

The nano-bonding wires provide superior electrical characteristics as well as mechanical strength in wire bonding applications. In a wire bonding process, one end of the nano bonding wire is melted by discharging to form a free air ball of a predetermined size and pressed on the chip pad to be bound to the chip pad. A loop of the nano bonding wire having an appropriate height and length is formed to reach a corresponding lead frame, and the other end of the bonding wire is bound to the lead frame with an application of pressure. As a result, the chip and the lead frame are electrically connected. For low cost production, the chip can be embedded inside a suitable epoxy. Alternatively, the chip can be embedded in a plastic flexible substrate that can interconnect a number of other chips. For example, in a plastic flexible credit card, a solar cell is mounted, printed or suitably positioned at a bottom layer to capture photons and convert the photons into energy to run the credit card operation. Display and processor electronics are then mounted or on a plastic substrate. A transceiver chip with nano antennas is also mounted or printed on the plastic substrate.

For high performance applications that generate large amounts of heat such as processor chips, the resulting chip is then bonding to a nano-ceramic housing to maximize heat radiation and to control chip temperature.

As discussed in US Application Serial No 20040029706, the content of which is incorporated by reference, methods are disclosed for using ceramic nanocomposites in applications requiring thermal barrier materials and in applications requiring material properties selected from the group consisting of thermally insulating, electrically conducting, mechanically robust, and combinations thereof. However, for certain electrical applications, thermal conductance is required.

In one embodiment of the present system, a heat conducting ceramic nanocomposite for removing unwanted heat is made with a ceramic host material and a nanostructured carbon material selected from the group consisting of carbon nanotubes, single-wall carbon nanotubes, vapor grown carbon fibers, fullerenes, buckyballs, carbon fibrils, buckyonions, metallofullerenes, endohedral fullerenes, and combinations thereof. In some embodiments, the nanostructured carbon material serves to increase the thermal conductivity of the ceramic host. In some embodiments, it does this by serving as a phonon concentrating center. In other embodiments, it increases the thermal conductivity by altering the structure of the ceramic host. In some embodiments of the present system, at least some of the nanostructured carbon material present imparts greater structural integrity to the ceramic host. A ceramic nanocomposite, according to the present system, can exist in the form of coatings, bulk objects, and combinations thereof. The ceramic host of the nanocomposite of the present system can be any ceramic which suitably provides for the nanocomposite material of the present system. Suitable ceramics include, but are not limited to, zirconia, alumina, silica, titania, yttria, ceria, boron nitride, carbon nitride, silicon nitride, silicon carbide, tantalum carbide, tungsten carbide, and combinations thereof. In some embodiments, the nanostructured carbon material comprises single-wall carbon nanotubes which may, or may not, be in the form of short "pipes." In some embodiments, the nanostructured carbon material is modified by a chemical means to yield derivatized nanostructured carbon material. Here, "derivatization" is taken to mean attachment of other chemical entities to the nanostructured carbon material. This attachment may be by chemical or physical means including, but not limited to, covalent bonding, van der Waals forces, electrostatic forces, physical entanglement, and combinations thereof. In other embodiments, the nanostructured carbon material is modified by a physical means selected from the group consisting of plasma treatment, heat treatment, ion bombardment, attrition by impact, milling and combinations thereof. In other embodiments, the nanostructured carbon material is modified by a chemical means selected from the group consisting of chemical etching by acids either in liquid or gaseous form, chemical etching by bases either in liquid or gaseous form, electrochemical treatments, and combinations thereof.

In another embodiment, the chip substrate can be in contact with several thin-film thermoelectric elements placed in parallel to heat or cool a particular area depending on the direction of current flow in these elements. Each thermoelectric nano-element has an n-type thermoelectric material, a p-type thermoelectric material located adjacent to the n-type thermoelectric material, a Peltier contact connecting the n-type thermoelectric material to the p-type thermoelectric material. Electrodes contact both a side of the n-type thermoelectric material opposite the Peltier contact and a side of the p-type thermoelectric material opposite the Peltier contact. Appropriately biased electrical current flow through selected ones of the thermoelectric elements makes the Peltier contact either a heated junction or a cooled junction. In another embodiment, only one leg of the thermoelectric element is required to produce heating or cooling. In this embodiment, a selected type of thermoelectric material (i.e. n-type or p-type) is utilized with the Peltier contact. Current flow in a first direction through an electrode, a thermoelectric material, the Peltier contact, and a subsequent electrode results in a heated junction at the Peltier contact. A current flow in a second direction opposite to the first produces a cooled junction at the Peltier contact. As disclosed in US Patent Application No. 20020174660, the content of which is incorporated by reference, a cantilever similar to arrangements known in the art for atomic force microscopy (AFM) can be used. The integration of a thermoelectric cooling/heating device or module with a cantilever, especially the cantilevers similar to those used in AFM, provides for "nanometer-size temperature control" of bio-tissues, cells, and perhaps other atomic-scale structures in nano technology such as for example nano-self-assembly.

In some embodiments of the present system, a method for making ceramic nanocomposites comprising a nanostructured carbon component and a ceramic host component includes preparing a slurry comprising ceramic particles and solvent; and adding nanostructured carbon materials such that they become dispersed in the slurry. The solvent used to prepare the slurry can be selected from the group consisting of aqueous solvents, non-aqueous solvent, and combinations thereof. Such solvents include, but are not limited to, water, toluene, ethyl alcohol, trichloroethylene, methyl ethyl ketone, and combinations thereof. In some embodiments, the step of preparing the slurry further comprises adding a dispersal agent. Such dispersal agents include, but are not limited to, natural formulations, synthetic formulations, polyelectrolyte dispersants, surfactants, wrapping polymers, and combinations thereof. In some embodiments, the step of preparing the slurry further comprises adding binding agents and/or plasticizers.

In some embodiments of the present system, the adding the nanostructured carbon materials (note that this step can be combined with the step of preparing the slurry) to the slurry further comprises the utilization of dispersion assistance to facilitate dispersion. In some embodiments, this step further comprises a milling operation, and possibly a nanomilling operation. In some embodiments of the present system, the slurry is shaped by a casting technique. Suitable casting techniques include, but are not limited to, tape casting, spin casting, solid casting, slip casting, robocasting, and combinations thereof. In some embodiments, the step of shape-forming comprises a gel casting technique. Here, a "sol-gel" technique is one which provides for a ceramic component first as a solution or "sol" of precursors which is hydrolyzed and polymerized into a "gel." Thus, the term, "sol-gel" represents the material at any stage of its transformation from a solution to a gel. The method of making coatings and objects can also include spraying these ceramic nanocomposite powders with a technique selected from the group consisting of plasma spraying, thermal spraying, powder spraying, electrostatically-assisted powder spraying, and combinations thereof.

In various embodiments, nano-elements can be formed in conjunction with nano-sized materials include, but are not limited to, ceramics, intermetallics, and metals. Other examples of nano-sized materials according to embodiments of the present invention include coated and encapsulated materials. Ceramic materials and intermetallics are often used to enhance, for example, the high-temperature mechanical strength of the nanocomposite material. In some embodiments the ceramic comprises an oxide, such as, for example, an oxide comprising at least one of aluminum, yttrium, zirconium, and cerium. In other embodiments, the ceramic comprises at least one of a carbide, a nitride, and a boride. In still other embodiments, the intermetallic comprises a silicide. In certain embodiments where the nano-sized material comprises a metal, the nano-sized metal has a melting temperature higher than that of the molten material such that the nano-sized metal remains substantially inert with respect to the molten metal. Metals with high melting points, for example, tungsten, are suitable as nano-sized materials for embodiments of this type. It will be appreciated by those skilled in the art that the choice of any specific combination of molten material and nano-sized material is based upon the combination of properties desired for the resultant nanocomposite material, including, but not limited to, physical, chemical, mechanical, electrical, magnetic, and thermal properties.

In one embodiment, an electronic device is formed with a nanocomposite material. The method includes providing a molten material; providing a nano-sized electronic device along with other nano-material, the nano-sized electronic device/material being substantially inert with respect to the molten material; introducing the nano-sized material into the molten material; dispersing the nano-sized material within the molten material using at least one dispersion technique selected from the group consisting of agitating the molten material using ultrasonic energy to disperse the nano-sized material within the molten material; introducing at least one active element into the molten material to enhance wetting of the nano-sized material by the molten material; and coating the nano-sized material with a wetting agent to promote wetting of the molten metal on the nano-sized material; and solidifying the molten material to form a solid nanocomposite material, the nanocomposite material comprising a dispersion of the nano-sized material within a solid matrix. Additional materials include those noted in US Application Serial No. 20040016318, the content of which is incorporated by reference. The electronic devices self-assemble inside the matrix after the dispersion. Such a nano-composite material with built-in transistors, processors, memories and other electronics forms intelligent articles such as medical prostheses, smart clothing, smart appliances and smart vehicles and smart robots, among others. These articles in turn are powered by nano fuel cells as disclosed in commonly owned patent application Ser. No. 11/064,363 and 11/064,366, the content of which is incorporated by reference.

The resulting composite material can be a nanocomposite magnet, a magnetic refrigerator element, an abrasion resistant surface coat, a higher-order structure piezoelectric element composed of a mixture of piezoelectric materials different in frequency response property, a heating element, a higher-order structure dielectric displaying the characteristics over a wide range of temperature, a photocatalyst material and the induction material thereof, a functional surface coat composed of a mixture of materials having such properties as the water holding property, hydrophilicity, and water repellency, a minute machine part, an abrasion resistant coat for a magnetic head, an electrostatic chuck, a sliding member material, an abrasion resistant coat of a die and mending the abraded and chipped parts thereof, an insulating coat of an electrostatic motor, an artificial bone, an artificial dental root, a condenser, an electronic circuit part, an oxygen sensor, an oxygen pump, a sliding part of a valve, a distortion gauge, a pressure-sensitive sensor, a piezoelectric actuator, a piezoelectric transformer, a piezoelectric buzzer, a piezoelectric filter, an optical shutter, an automobile knock sensor, a supersonic sensor, an infrared sensor, an antivibration plate, a cutting machining tool, a surface coat of a copying machine drum, a polycrystalline solar cell, a dye sensitization type solar cell, a surface coat of a kitchen knife or a knife, the ball of a ball point pen, a temperature sensor, the insulation coat of a display, a superconductor thin film, a Josephson element, a super plastic structure body, a ceramic heating element, a microwave dielectric, a water-repellent coat, an antireflection film, a heat ray reflecting film, a UV absorbing film, an inter-metal dielectric layer (IMD), a shallow trench isolation (STI), and the like. In various embodiments, nano-elements such as FSAs are used as fillers in a variety of pure phase materials such as polymers that are now readily available at low cost. The nanofiller may be mixed with a monomer, which is then polymerized to form a polymer matrix composite. In another embodiment, the nanofiller may be mixed with a matrix powder composition and compacted to form a solid composite. In yet another embodiment, the matrix composition may be dissolved in a solvent and mixed with the nanofiller, and then the solvent may be removed to form a solid composite. In still another embodiment, the matrix may be a liquid or have liquid like properties. The nano-fillers improve the properties of the low cost pure phase materials including, for example, electrical conductivity, magnetic permeability, dielectric constant, and thermal conductivity. A matrix is blended with a filler material with desirable properties that can include refractive index, transparency to light, reflection characteristics, resistivity, permittivity, permeability, coercivity, B—H product, magnetic hysteresis, breakdown voltage, skin depth, curie temperature, dissipation factor, work function, band gap, electromagnetic shielding effectiveness, radiation hardness, chemical reactivity, thermal conductivity, temperature coefficient of an electrical property, voltage coefficient of an electrical property, thermal shock resistance, biocompatibility, and/or wear rate. The desired material property is selected from the group consisting of refractive index, transparency to light, reflection characteristics, resistivity, permittivity, permeability, coercivity, B—H product, magnetic hysteresis, breakdown voltage, skin depth, curie temperature, dissipation factor, work function, band gap, electromagnetic shielding effectiveness, radiation hardness, chemical reactivity, thermal conductivity, temperature coefficient of an electrical property, voltage coefficient of an electrical property, thermal shock resistance, biocompatibility and wear rate. The nanostructured filler may comprise one or more elements selected from the s, p, d, and f groups of the periodic table, or it may comprise a compound of one or more such elements with one or more suitable anions, such as aluminum, antimony, boron, bromine, carbon, chlorine, fluorine, germanium, hydrogen, indium, iodine, nickel, nitrogen, oxygen, phosphorus, selenium, silicon, sulfur, or tellurium. The matrix may be a polymer (e.g., poly(methyl methacrylate), poly(vinyl alcohol), polycarbonate, polyalkene, or polyaryl), a ceramic (e.g., zinc oxide, indium-tin oxide, hafnium carbide, or ferrite), or a metal (e.g., copper, tin, zinc, or iron).

Other filler materials include those in Application Serial No. 20030207978, the content of which is incorporated by reference.

Energy Source

Figure 10:
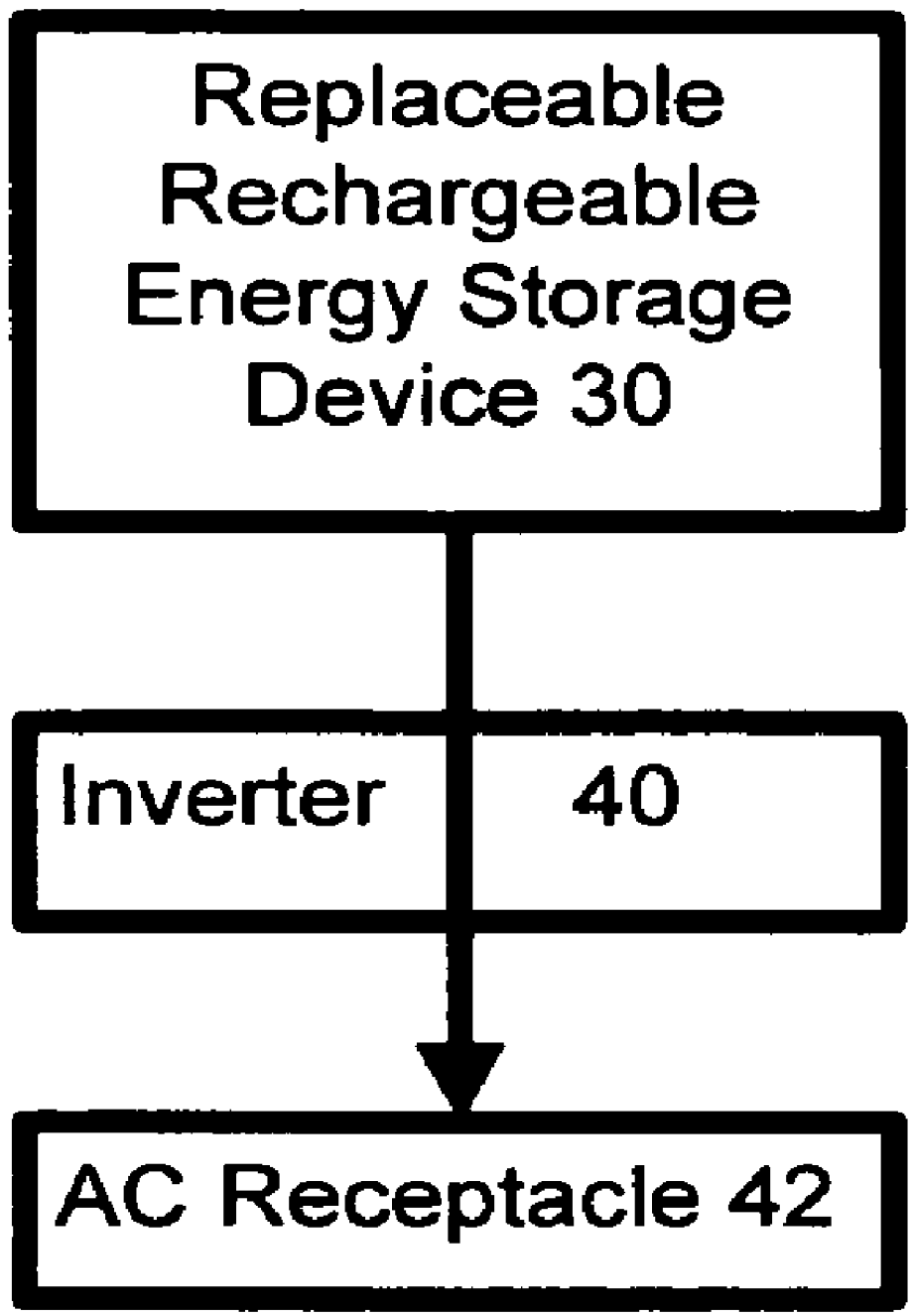
FIG. 10 shows an exemplary power generation system.

FIG. 10 shows one embodiment of a mobile power unit 1. The unit 1 has one or more fuel cells 30. The output of the fuel cells is direct current (DC) which is provided to an inverter 40 for generating AC voltages to operate mobile equipment. Since the fuel cell 30 compactly stores large quantity of energy, the entire mobile power unit 1 is approximately the size of a cigarette pack and yet can power AC equipment in the field for days. When the fuel cells 30 are depleted, they can be refueled in situ, thus allowing the AC equipment to operate without interruption.

Fuel cells enable the electrochemical conversion of fuel gases and oxygen into oxidized products and electrical energy. The difference from traditional chemical processes consists of performing reduction and oxidation of the components, separately, at two electrodes. Chemical reaction of the reactants at the electrodes occurs because ionic conduction is ensured via a gas-tight electrolyte, and the transport of electrons takes place only via an external circuit. The hydrogen is obtained from fossil fuels. Typical representatives of these fuels are natural gas, methanol and aliphatic or aromatic hydrocarbons, as well as mixtures thereof, such as, for example, petrol and diesel oil. In principle, it is also possible to produce the hydrogen-containing fuel gas biologically and directly as synthesis gas and to work it up in an appropriate manner for use in a fuel cell. Methanol can also be produced biologically, for example, with the aid of methylotrophic yeasts.

In one embodiment, the cell 30 stores hydrogen which has previously been produced from electricity and water. The cell 30 is a cost-effective and pollution-free energy storage device. Different types of fuel cells including proton exchange membranes, solid oxides, high temperature fuel cells, and regenerative fuel cells can be used. In one embodiment, a proton exchange membrane (PEM) fuel cell includes an anode, a cathode, and a selective electrolytic membrane disposed between the two electrodes. In a catalyzed reaction, a fuel such as hydrogen is oxidized at the anode to form cations (protons) and electrons. The ion exchange membrane facilitates the migration of protons from the anode to the cathode. The electrons cannot pass through the membrane and are forced to flow through an external circuit thus providing an electrical current. At the cathode, oxygen reacts at the catalyst layer, with electrons returned from the electrical circuit, to form anions. The anions formed at the cathode react with the protons that have crossed the membrane to form liquid water as the reaction product. Typically, a combustion reaction is not involved. Accordingly, fuel cells are clean and efficient.

The hydrogen in the fuel cell 30 can also move through an active transport membrane (ATM). In the ATM embodiment, the fuel cell 30 employs molecules used in biological processes to create fuel cells that operate at moderate temperatures and without the presence of harsh chemicals maintained at high temperatures, which can lead to corrosion of the cell components. The compact, inert energy sources can be used to provide short duration electrical output. Since the materials retained within the fuel cells are non-corrosive and typically not otherwise hazardous, it is practical to recharge the fuel cells with fuel, with the recharging done by the user. Alternatively, the fuel cells 30 can be electrically re-charged.

In one embodiment, the fuel cell includes a first compartment with an electron carrier in communication with redox enzymes to deliver electrons to a first electrode; a second compartment having an electron receiving composition in chemical communication with a second electrode, and a barrier separating the first compartment from the second compartment; said barrier having embedded proton transporting proteins effective to transport protons from the first compartment to the second compartment. During operation, an electrical current flows along a conductive pathway formed between the first electrode and the second electrode.

The first compartment can include an electron transfer mediator that transfers electrons from the redox enzymes to the first electrode. The proton transporting proteins include redox enzyme activity. A reservoir can be used for supplying to the vicinity of at least one of the electrodes a component consumed in the operation of the fuel cell and a pump for drawing such component to that vicinity.

As discussed in U.S. Pat. No. 6,500,571, the content of which is incorporated by reference, examples of particularly preferred enzymes providing one or both of the oxidation/reduction and proton pumping functions include, for example, NADH dehydrogenase (e.g., from *E. coli*. Tran et al., "Requirement for the proton pumping NADH dehydrogenase I of *Escherichia coli* in respiration of NADH to fumarate and its bioenergetic implications," Eur. J. Biochem. 244: 155, 1997), NADPH transhydrogenase, proton ATPase, and cytochrome oxidase and its various forms. Methods of isolating such an NADH dehydrogenase enzyme are described in detail, for example, in Braun et al., Biochemistry 37: 1861-1867, 1998; and Bergsma et al., "Purification and characterization of NADH dehydrogenase from *Bacillus subtilis*," Eur. J. Biochem. 128: 151-157, 1982. The lipid bilayer can be formed across the perforations 49 and enzyme incorporated therein by, for example, the methods described in detail in Niki et al., U.S. Pat. No. 4,541,908 (annealing cytochrome C to an electrode) and Persson et al., J. Electroanalytical Chem. 292: 115, 1990. Such methods can comprise the steps of: making an appropriate solution of lipid and enzyme, where the enzyme may be supplied to the mixture in a solution stabilized with a detergent; and, once an appropriate solution of lipid and enzyme is made, the perforated dielectric substrate is dipped into the solution to form the enzyme-containing lipid bilayers. Sonication or detergent dilution may be required to facilitate enzyme incorporation into a bilayer. See, for example, Singer, Biochemical Pharmacology 31: 527-534, 1982; Madden, "Current concepts in membrane protein reconstitution," Chem. Phys. Lipids 40: 207-222, 1986; Montal et al., "Functional reassembly of membrane proteins in planar lipid bilayers," Quart. Rev. Biophys. 14: 1-79, 1981; Helenius et al., "Asymmetric and symmetric membrane reconstitution by detergent elimination," Eur. J. Biochem. 116: 27-31, 1981; Volumes on biomembranes (e.g., Fleischer and Packer (eds.)), in Methods in Enzymology series, Academic Press.

Using enzymes having both the oxidation/reduction and proton pumping functions, and which consume electron carrier, the acidification of the fuel side caused by the consumption of electron carrier is substantially offset by the export of protons. Net proton pumping in conjunction with reduction of an electron carrier can exceed 2 protons per electron transfer (e.g., up to 3 to 4 protons per electron transfer). Accordingly, in some embodiments care must be taken to buffer or accommodate excess de-acidification on the fuel side or excess acidification of the product side. Alternatively, the rate of transport is adjusted by incorporating a mix of redox enzymes, some portion of which enzymes do not exhibit coordinate proton transport. In some embodiments, care is taken especially on the fuel side to moderate proton export to match proton production. Acidification or de-acidification on one side or another of the fuel cell can also be moderated by selecting or mixing redox enzymes to provide a desired amount of proton production. Of course, proton export from the fuel side is to a certain degree self-limiting, such that in some embodiments the theoretical concern for excess pumping to the product side is of, at best, limited consequence. For example, mitochondrial matrix proteins which oxidize electron carriers and transport protons operate to create a substantial pH gradient across the inner mitochondrial membrane, and are designed to operate as pumping creates a relatively high pH such as pH 8 or higher. (In some embodiments, however, care is taken to keep the pH in a range closer to pH 7.4, where many electron carriers such as NADH are more stable.) Irrespective of how perfectly proton production is matched to proton consumption, the proton pumping provided by this embodiment of the invention helps diminish loses in the electron transfer rate due to a shortfall of protons on the product side. In some embodiments, proton pumping is provided by a light-driven proton pump such as bacteriorhodopsin. Recombinant production of bacteriorhodopsin is described, for example, in Nassal et al., J. Biol. Chem. 262: 9264-70, 1987. All trans retinal is associated with bacteriorhodopsin to provide the light-absorbing chromophore. Light to power this type of proton pump can be provided by electronic light sources, such as LEDs, incorporated into the fuel cell and powered by a (i) portion of energy produced from the fuel cell, or (ii) a translucent portion of the fuel cell casing that allows light from room lighting or sunlight to impinge the lipid bilayer.

The fuel cell operates within a temperature range appropriate for the operation of the redox enzyme. This temperature range typically varies with the stability of the enzyme, and the source of the enzyme. To increase the appropriate temperature range, one can select the appropriate redox enzyme from a thermophilic organism, such as a microorganism isolated from a volcanic vent or hot spring. Nonetheless, preferred temperatures of operation of at least the first electrode are about 80.degree.C. or less, preferably 60.degree.C. or less, more preferably 40.degree.C. or 30.degree.C. or less. The porous matrix is, for example, made up of inert fibers such as asbestos, sintered materials such as sintered glass or beads of inert material.

The first electrode (anode) can be coated with an electron transfer mediator such as an organometallic compound which functions as a substitute electron recipient for the biological substrate of the redox enzyme. Similarly, the lipid bilayer of the embodiment of FIG. 3 or structures adjacent to the bilayer can incorporate such electron transfer mediators. Such organometallic compounds can include, without limitation, dicyclopentadienyliron ($C_{10}H_{10}Fe$, ferrocene), available along with analogs that can be substituted, from Aldrich, Milwaukee, Wis., platinum on carbon, and palladium on carbon. Further examples include ferredoxin molecules of appropriate oxidation/reduction potential, such as the ferredoxin formed of rubredoxin and other ferredoxins available from Sigma Chemical. Other electron transfer mediators include organic compounds such as quinone and related compounds. The electron transfer mediator can be applied, for example, by screening or masked dip coating or sublimation. The first electrode can be impregnated with the redox enzyme, which can be applied before or after the electron transfer mediator. One way to assure the association of the redox enzyme with the electrode is simply to incubate a solution of the redox enzyme with electrode for sufficient time to allow associations between the electrode and the enzyme, such as Van der Waals associations, to mature. Attentively, a first binding moiety, such as biotin or its binding complement avidin/streptavidin, can be attached to the electrode and the enzyme bound to the first binding moiety through an attached molecule of the binding complement.

The redox enzyme can comprise any number of enzymes that use an electron carrier as a substrate, irrespective of whether the primary biologically relevant direction of reaction is for the consumption or production of such reduced electron carrier, since such reactions can be conducted in the reverse direction. Examples of redox enzymes further include, without limitation, glucose oxidase (using NADH, available from several sources, including number of types of this enzyme available from Sigma Chemical), glucose-6-phosphate dehydrogenase (NADPH, Boehringer Mannheim, Indianapolis, Ind.), 6-phosphogluconate dehydrogenase (NADPH, Boehringer Mannheim), malate dehydrogenase (NADH, Boehringer Mannheim), glyceraldehyde-3-phosphate dehydrogenase (NADH, Sigma, Boehringer Mannheim), isocitrate dehydrogenase (NADH, Boehringer Mannheim; NADPH, Sigma), and .alpha.-ketoglutarate dehydrogenase complex (NADH, Sigma).

The redox enzyme can also be a transmembrane pump, such as a proton pump, that operates using an electron carrier as the energy source. In this case, enzyme can be associated with the electrode in the presence of detergent and/or lipid carrier molecules which stabilize the active conformation of the enzyme. As in other embodiments, an electron transfer mediator can be used to increase the efficiency of electron transfer to the electrode.

Associated electron carriers are readily available from commercial suppliers such as Sigma and Boehringer Mannheim. The concentrations at which the reduced form of such electron carriers can be as high as possible without disrupting the function of the redox enzyme. The salt and buffer conditions are designed based on, as a starting point, the ample available knowledge of appropriate conditions for the redox enzyme. Such enzyme conditions are typically available, for example, from suppliers of such enzymes.

In another embodiment where the fuel cells 30 need to be physically replaced while the AC equipment is running, the inverter 40 receives a back-up energy source such as a small battery or a high capacity capacitor. A current sensor is provided to sense current from the battery unit 30. Once the current is interrupted during operation indicating that the energy storage units are being replaced or that it has lost power, the inverter is connected to the back up energy source by a solid state switch or a relay. In this manner, the user-replaceable battery units 30 can be substituted in the field without interrupting power to the appliance by using the back-up energy source. The inverter 40 receives a low DC voltage input in electrical communication and provides a source of high DC voltage. The AC voltage to an appliance may be by an electrical lead directly from the voltage converter to the appliance or via a switch mechanism or an electrical plug or socket. In one embodiment, a standard AC wall plug connected to the inverter 40 operably supplies the high DC voltage to an appliance.

The back-up energy storage device can also be a conventional battery or a supercapacitor, which is a component intermediate between a capacitor and a battery in terms of energy and power. The supercapacitor can be any electrochemical system using at least the surface properties of an ideally polarizable material of high specific surface area. In other words, the super-capacitor is an electrochemical capacitor of high capacitance.

During charging of the supercapacitor, there is a build-up of ionic species on either side of the two electrodes, at the ideally polarizable material/electrolyte interface. There may also be oxidation-reduction reactions in the presence of redox sites, resulting in a pseudocapacitive system. Supercapacitors based on the principle of the double layer have been manufactured from a variety of materials. These supercapacitors are assembled from two carbon electrodes having a high specific surface area. In general, the capacitors include current leads, a separator lying between the electrodes, an electrolyte and a package sealed with respect to the environment. One component of a supercapacitor consists of the electrolyte which, typically, comprises a solution of a salt, that is to say a combination of a salt and a solvent. In general, the electrolytes are low-viscosity liquids and have a high conductivity over a wide temperature range. They must also be of low cost, chemically and electrochemically stable and compatible with carbon or the other materials of which the electrodes are composed.

One exemplary super-capacitor is disclosed in U.S. Pat. No. 6,671,166, the content of which is incorporated by reference. As discussed therein, a high power capacitor ideally polarizable has a positive electrode and its current collector, a negative electrode and its current collector, said electrodes comprising a carbon containing material with high specific surface area, a separator and a non-aqueous liquid electrolyte impregnating said separator and said electrodes. The non-aqueous liquid electrolyte is an organic solution of a sodium or potassium or alkalin-earth metal salt, on their own or mixed in a solvent containing an acid.

The inverter 40 can be a step-up transformer capable of amplifying low DC voltage to high DC voltage. The term "low voltage DC" generally encompasses voltages within the range from about 5 volts to about 50 volts DC and more preferably from about 6 volts to about 36 volts DC and even more preferably from about 8 volts to about 24 volts DC. Particularly preferred low voltages are about 8, 12, 24 or 36 volts with a variation of about 4 volts. High voltage AC encompasses voltages within the range from about 280 to about 480 volts AC. At high voltage levels power may be supplied over long distances with a voltage drop with minimal adverse effect on the system. As a result, the user can effectively power an end appliance at a great distance from the power source and portable converter. This is advantageous in a situation where a mobile appliance is energized by the system. The mobile power unit and the appliance, singly or in combination, may be moved widely and freely.

In one embodiment, the inverter can be pulse-width modulated inverter. A PWM inverter is controlled by a control circuit, and the output of the PWM inverter is supplied to a sine wave filter (LC low-pass filter). The sine filter includes an LC filter composed of a reactor and a capacitor, and a damping circuit which is a serial circuit of a resistor and a capacitor. The damping circuit is connected in parallel with the capacitor in order to limit oscillation waveforms accompanying the resonance of the reactor and the capacitor. The control circuit comprises a mean value circuit, an automatic voltage regulator (AVR), an instantaneous voltage command value generator, and a PWM signal generator. First, a voltage detector is connected to the output of the sine filter to detect the instantaneous output voltage V of the sine filter. The output voltage V is inputted to the mean value circuit. The mean value circuit produces the mean value of the instantaneous output voltage. The mean value is subtracted from a predetermined voltage reference value by a summing point, and the difference is supplied to the automatic voltage regulator. The automatic voltage regulator corrects the voltage reference value so that the difference becomes zero, and supplies the resultant corrected voltage reference value to the instantaneous voltage command value generator. The instantaneous voltage command value generator, receiving the corrected voltage reference value VA and a predetermined frequency reference value, generates a sinusoidal instantaneous voltage command value having amplitude determined by the corrected voltage reference value VA and a frequency determined by the frequency reference value. The output voltage V is subtracted from the instantaneous voltage command value by a summing point 82, and the difference is provided to a gain adjuster. The output of the gain adjuster is added to the voltage command value by a summing point that outputs a corrected voltage command value to the PWM signal generator. The PWM signal generator outputs a pulse signal corresponding to the corrected voltage command value and controls the PWM inverter by the pulse signal. The foregoing describes the control of one PWM inverter in one embodiment. In another embodiment, a plurality of PWM inverters can be connected in parallel to supply power to a common load.

In one embodiment, the fuel cell 30 has a microcontroller embedded therein. The microcontroller provides the appliance with various information items such as fuel cell conditions, fuel cell charge capacity, and a manufacturing company of the fuel cell. Typically, communications between the fuel cell microcontroller and the appliance are done over a serial RS-232 protocol. Other protocols include Universal Serial Bus (USB), SCSI, or Firewire. In this manner, the smart fuel cell can provide information about its residual capacity to the appliance so as to display a fuel cell state relevant to the residual capacity of the fuel cell.

As described above, while the smart fuel cell has a function of offering the information on the residual amount of fuel cell capacity, and it is required to exactly estimate the fuel cell capacity changeable in accordance with various environmental elements in order to offer exact fuel cell residual capacity information. Thus, the smart fuel cell sets up a new reference capacity in accordance with the changes of fuel cell capacity, and provides present residual capacity information based on the reference capacity. For the purpose of establishing the new reference capacity, the smart fuel cell carries out calibration when an output voltage becomes lower than a predetermined level. The calibration is used for re-establishing the reference capacity of the fuel cell with a measured value of a total charge capacity of a fuel cell. During the calibration, a discharge starts from a full-charged state, and the amount discharged until the output voltage of the smart fuel cell becomes lower than the predetermined voltage level is established as a reference capacity. In case that the fuel cell continues to be discharged after the calibration, the reference capacity is set by performing a re-calibration after the former discharge is finished.

In one embodiment where the appliance is a computer, a power management software detects a state of low fuel cell (LB) in which the fuel cell residual capacity is reduced less than 10%, and displays a warning for a user. Then, if the smart fuel cell continues to discharge, and thus a low low fuel cell voltage is detected, i.e. if the fuel cell residual capacity is reduced less than a predetermined amount, e.g., less than 3%, the power management system stores data by making an operating system (OS) program to protect current data at work. This case is called a low low fuel cell (LLB) state. The OS program serves to support a power management function such as advanced power manager (APM) or advanced configuration and power interface (ACPI), and for instance, a WINDOWS type of OS (operating system) of the MICROSOFT Corporation belongs to the program. The OS program allows the data being processed of the present system to be stored in a hard disk drive, and after the operation, the power management system finishes the system by blocking the power source provided from the smart fuel cell. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

What is claimed is:

1. A memory device, comprising:
   an array of memory structures disposed in rows and columns and constructed over a substrate, each memory structure comprising a first signal electrode, a second signal electrode, and a resistive layer coupled to the first signal electrode and the second signal electrode;
   a plurality of word lines connected to the first signal electrodes of a row of memory cells; and
   a plurality of bit lines connected to the second signal electrodes of a column of memory cells and wherein the resistive layer comprises two resistive elements that in combination have a zero temperature coefficient.

2. The memory device of claim 1, wherein the resistive layer comprises memory elements.

3. The memory device of claim 1, further comprising a driver circuit for selectively controlling the first signal electrodes or the second signal electrodes.

4. The memory device of claim 3, wherein the circuit includes one or more of a Y gate, a sense amplifier, an input-output buffer, an X address decoder, a Y address decoder, and an address buffer.

5. The memory device of claim 1, wherein the substrate includes a silicon-on-insulator wafer.

6. The memory device of claim 1, wherein the resistive layer is spin-coated over the substrate wherein first signal electrodes and the second signal electrodes are constructed.

7. The memory device of claim 1, wherein the resistive layer includes stacked layers.

8. The memory device of claim 1, wherein the resistive layer forms transistors.

9. The memory device of claim 1, wherein the resistive layer store data at intersections of resistors.

10. The memory device of claim 1, further comprising an array of redundant memory elements.

11. The memory device of claim 10, wherein the redundant array is a row or a column of redundant resistive-elements.

12. The memory device of claim 1, comprising magnetic elements or optical elements coupled to the memory.

13. The memory device of claim 1, further comprising memory devices forming a plurality of memory hierarchy to optimize data access speed.

14. A memory electronic device, comprising:
    a substrate;
    a first layer fabricated using semiconductor fabrication techniques;
    a second layer formed above the first layer, the second layer having one or more resistive-bonding areas;
    one or more resistive memory elements self-assembled to the second layer resistive bonding areas and wherein the resistive memory elements comprises two resistive elements that in combination have a zero temperature coefficient.

15. The device of claim 14, wherein the resistive-elements is disposed in an array pattern.

16. The device of claim 14, wherein the resistive-elements are spin-coated on the second layer.

17. A memory electronic device, comprising:
    a substrate;
    a first layer fabricated using semiconductor fabrication techniques;
    a second layer formed above the first layer, the second layer having one or more resistive-bonding areas;
    a plurality of resistive memory elements coupled to the second layer resistive bonding areas, wherein each resistive memory element has two resistive elements that in combination has a zero temperature coefficient.

18. The device of claim 17, wherein a first resistive element comprises a positive temperature coefficient and the second resistive element has a negative temperature coefficient.

19. The device of claim 17, wherein the temperature coefficient is selected such that a series or parallel combination of the two elements results in a resistive element having zero temperature coefficient.

* * * * *